(12) United States Patent
Sakairi

(10) Patent No.: US 8,368,011 B2
(45) Date of Patent: Feb. 5, 2013

(54) ION DETECTOR

(75) Inventor: Minoru Sakairi, Tokorozawa (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 13/264,604

(22) PCT Filed: Apr. 17, 2009

(86) PCT No.: PCT/JP2009/057763
§ 371 (c)(1),
(2), (4) Date: Oct. 14, 2011

(87) PCT Pub. No.: WO2010/119568
PCT Pub. Date: Oct. 21, 2010

(65) Prior Publication Data
US 2012/0037799 A1   Feb. 16, 2012

(51) Int. Cl.
*H01J 49/04*   (2006.01)
(52) U.S. Cl. .................... 250/286; 250/283; 250/397
(58) Field of Classification Search .......... 250/286, 250/283, 397
See application file for complete search history.

(56) References Cited

U.S. PATENT DOCUMENTS

| | | | |
|---|---|---|---|
| 5,153,520 A * | 10/1992 | Dumbeck | 324/469 |
| 6,177,668 B1 | 1/2001 | Hager | |
| 6,278,111 B1 | 8/2001 | Sheehan et al. | |
| 2004/0031917 A1 | 2/2004 | Hager | |
| 2004/0079879 A1 | 4/2004 | Ross et al. | |
| 2004/0206910 A1 | 10/2004 | Lee et al. | |
| 2005/0145789 A1 | 7/2005 | Miller et al. | |
| 2011/0097812 A1 * | 4/2011 | Bather et al. | 436/153 |

FOREIGN PATENT DOCUMENTS

| | | |
|---|---|---|
| JP | 07-325020 | 12/1995 |
| JP | 2000-510638 | 8/2000 |
| JP | 2003-514349 | 4/2003 |
| JP | 2003-257328 | 9/2003 |
| JP | 2004-528685 | 9/2004 |
| JP | 2006-510905 | 3/2006 |

OTHER PUBLICATIONS

International Search Report and Written Opinion for PCT International Application No. PCT/JP2009/057763, mailed May 19, 2009.
J.I. Baumbach, "Process Analysis using Ion Mobility Spectrometry", Anal. Bioanal. Chem. (2005) vol. 384, No. 5, pp. 1059-1070.

* cited by examiner

*Primary Examiner* — Kiet T Nguyen
(74) *Attorney, Agent, or Firm* — Brundidge & Stanger, P.C.

(57) ABSTRACT

By detecting water clusters in expiration with high sensitivity, prevention of drink-driving and prevention of drowsy driving are performed. Also, device operation is performed in a non-contact manner. Problem: an effective method for prevention of drink-driving and prevention of drowsy driving for drivers has not been present. Effect: expiration can be sensed in a spatially-restricted place.

10 Claims, 33 Drawing Sheets

DATA PROCESSOR

PEAKS ASSOCIATED WITH EXPIRATION

PEAKS ASSOCIATED WITH EXPIRATION

ION DETECTOR

TECHNICAL FIELD

The present invention relates to a detector on the basis of ion detection under atmospheric pressure. Also, the present invention relates to an alcohol detector and a preventive device for drowsy driving in a movable body such as an automobile, with expiration detection technology as a base. Furthermore, the present invention relates to a non-contact device interface, an analysis preprocessor, and a breath training device.

BACKGROUND ART

In the field of existing technologies such as expiration detection, detection of alcohol in expiration, detection of drowsing, device interface, and analysis, there is a method of ionizing a target substance for detection by a mass analyzing unit that is present in a vacuum.

A method disclosed in Patent Document 1 is a method of introducing minute droplets generated by an ionizing method called an electrospray method to a second chamber in a vacuum, promoting desolvation by a collision with gas introduced from above in that chamber, and performing a mass analysis on the desolvated ions.

In a method disclosed in Patent Document 2, a current of ions generated under atmospheric pressure flowing into a skimmer cone under a vacuum and/or a lens electrode of a subsequent ion converging lens system is detected, and the applied voltage of the electrode is controlled so that the ion current is constant.

In a method described in Patent Document 3, ions generated in a vacuum are considerably deflected to collide with an electrode for optical system cleaning.

A method described in Patent Document 4 is a method of aerodynamically converging ions to be introduced in a vacuum.

A method described in Patent Document 5 relates to an ion trap type mass spectrometer for efficiently trapping ions in a vacuum.

A method described in Patent Document 6 is a method for improving an S/N ratio of a detection signal in a tandem mass spectrometer using an atmospheric ionization method.

In any case of the above, it is a major premise that ions are introduced in a vacuum for detection.
Prior Art Documents
Patent Documents
    Patent Document 1: U.S. Pat. No. 6,278,111
    Patent Document 2: Japanese Patent Application Laid-Open Publication No. 07-325020
    Patent Document 3: Japanese Patent Application Laid-Open Publication No. 2003-257328
    Patent Document 4: Japanese Patent Application Laid-Open Publication No. 2006-510905
    Patent Document 5: Japanese Patent Application Laid-Open Publication No. 2000-510638
    Patent Document 6: US 2004031917

SUMMARY OF THE INVENTION

Problems to be Solved by the Invention

In any method of the above, a mass spectrometer operating under a high vacuum is used for analyzing generated ions. With the use of the mass spectrometer, the mass number of ions can be measured, and highly accurate analysis can be carried out. However, for the mass spectrometer, a high vacuum of $10^{-4}$ Torr or lower is indispensable and, for this reason, a vacuum exhaust system such as a turbo-molecular pump or a rotary pump is provided, thereby disadvantageously increasing the size of the device, and that has been a major problem.

Means for Solving the Problem

In the existing technology, a vacuum exhaust system is provided to operate a mass spectrometer, thereby increasing the size of the device.

Here, if a portion where ions are detected is also operated under an atmospheric pressure in addition to a place where ions are generated, no vacuum exhaust system is required, and the size of the device can be significantly decreased, thereby solving the problem.

As a method of detecting ions under an atmospheric pressure, for example, the following method can achieve detection of expiration, which is outside air. Under an atmospheric pressure, an ion beam is generated by corona discharge or the like, and water clusters from expiration are introduced into the ion beam to cause a reaction with ions in the ion beam to generate water cluster ions. Under the atmospheric pressure, a downward motion is added to the water cluster ions by their force of gravitation, resulting in deflection of the water ion beam. Therefore, by measuring the amount of current of the deflected water cluster ion beam, expiration detection can be achieved.

Effects of the Invention

If outside air can be detected with a simple method, expiration can be sensed in a spatially-restricted place. For example, in an automobile, it is possible to prevent drink-driving based on a test of alcohol in expiration and prevent drowsy driving with a non-contact measurement of expiration.

Also, an interface for achieving device operation in a non-contact manner can be provided.

Furthermore, development into an analysis preprocessor and a breath training device can also be possible.

BRIEF DESCRIPTIONS OF THE DRAWINGS

BEST MODE FOR CARRYING OUT THE INVENTION

First Embodiment

In the present embodiment, an example of monitoring expiration, which is outside air, in a non-contact and noninvasive manner is described.

In expiration, water at a saturated vapor pressure level at approximately 37° C. is contained, and therefore water in expiration is released substantially as water clusters to the outside of the body. Here, when expiration is introduced to an ion beam at a microampere level under an atmospheric pressure generated by corona discharge from side surfaces of the ion beam, the water clusters are reacted with the ions in the ion beam to generate water cluster ions. The water cluster ions with their weight increased due to addition of the clusters cannot proceed straight ahead in an electric field under an atmospheric pressure, a downward force acts due to the force of gravitation, and part of the water cluster ion beam is considerably deflected. By measuring the amount of current of this deflected ion beam, expiration can be indirectly monitored.

Figure 1:
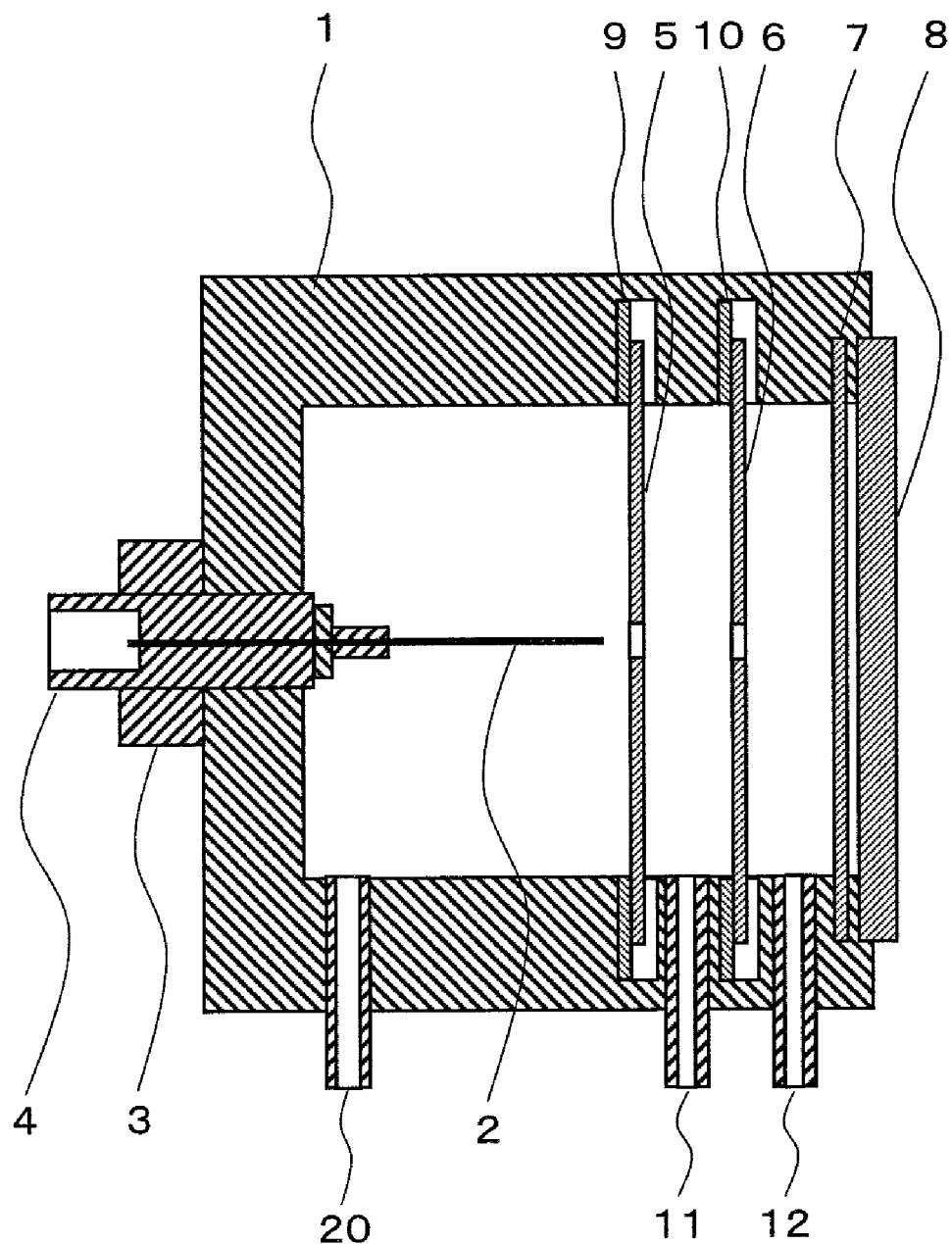
FIG. 1 is a structural diagram of a device of the present invention.
Figure 2:
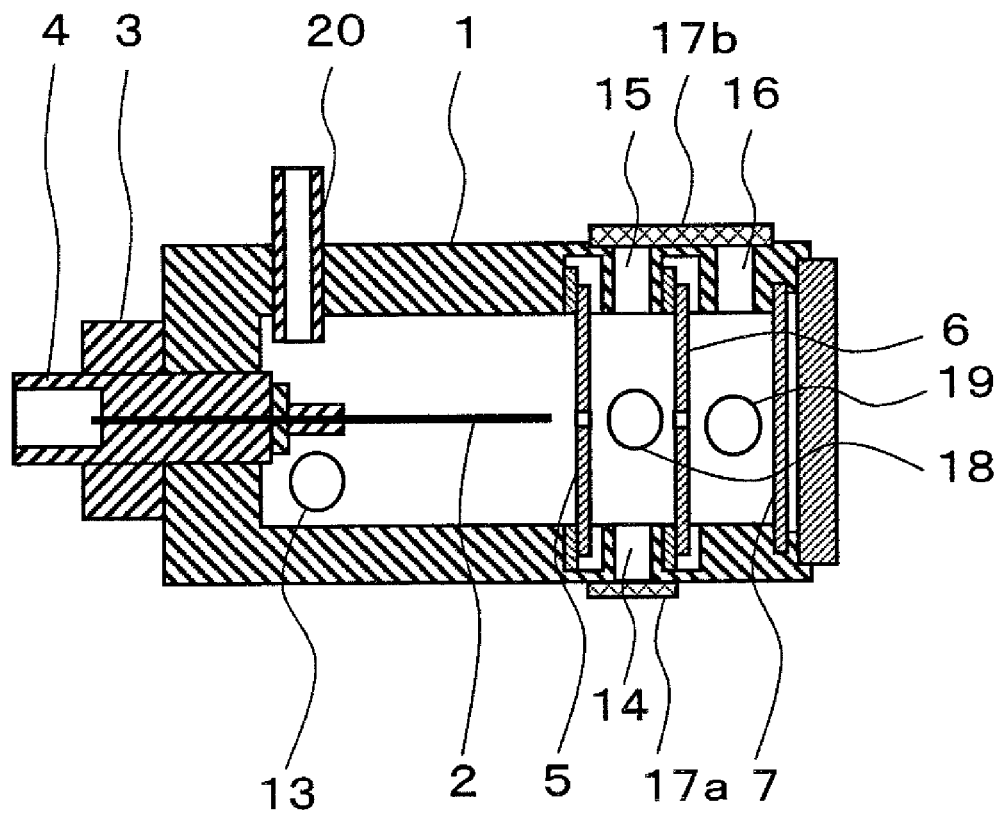
FIG. 2 is a structural diagram from a different angle of the device of the present invention.

Means for measuring the amount of current of an ion beam released from an ion source and deflected is depicted in FIGS. 1 and 2. FIGS. 1 and 2 are diagrams with their viewpoints changed at 90 degrees. When a high voltage is applied to a needle electrode for corona discharge 2 supported by a needle electrode for corona discharge holder 4 and a holder presser 3, a corona discharge is generated between the needle electrode and a counter electrode 5 supported by a counter-electrode support 9, and an ion beam is drawn from an opening of the counter electrode 5. Note that application of a high voltage to the needle electrode for corona discharge 2 may be performed via a control unit.

As the needle electrode for corona discharge 2, in addition to a tip portion pointed in a sewing needle shape, a metal material such as tungsten subjected to mechanical polishing or electrochemical polishing can be used. In particular, in the one subjected to electrochemical polishing, the radius of curvature of the needle electrode tip can be made on the order of 50 nanometers, and therefore corona discharge can be conveniently generated with a lower voltage.

Furthermore, with control by the control unit so that a potential difference is provided between the counter electrode 5 and a detection electrode 6 supported by a detection-electrode support 10, force from the counter electrode 5 to the detection electrode 6 is exerted onto the generated ion beam. When expiration containing water clusters is not introduced, the ion beam from the opening of the counter electrode 5 proceeds straight ahead while colliding with molecules in the atmosphere to spread in a cone shape, with only its perimeter colliding with the detection electrode 6 and being partially detected.

For example, when the counter electrode 5 with an opening having a diameter on the order of 3 mm is disposed at about 3 mm from the tip of the needle electrode for corona discharge 2 and a corona discharge current is generated on the order of 5 microamperes, an ion beam having a diameter on the order of 6 mm appears at the position of the counter electrode 5. In this case, at the detection electrode 6, a perimeter portion of the ion beam (a portion having a diameter on the order of 3 mm or larger up to a diameter on the order of 6 mm) is detected. In the conditions as described above, the current to be detected by the detection electrode 6 is equal to or smaller than several microamperes. Ions passing through the opening of the detection electrode 6 collide with a grounded stop electrode 7 and disappear. In this case, it is effective to ground the stop electrode 7. Also, it poses no problem to leave the end open without providing the stop electrode.

On the other hand, when expiration containing a large amount of water clusters is introduced to the ion beam flowing between the counter electrode 5 and the detection electrode 6 from a direction perpendicular to the paper plane of FIG. 1 toward the paper plane, the ion beam reacts with the water clusters in expiration to become water cluster ions. With an increase in weight, force acts in a direction of the force of gravitation for deflection, and the amount of current of the ion beam to be detected by the detection electrode 6 is increased compared with the case in which expiration is not introduced. As a matter of course, the amount of deflection differs depending on the size of each water cluster ion. Here, to reduce contamination of the tip portion of the needle electrode for corona discharge 2, it is effective in view of enhancement of longevity of the ion source to generate an air flow toward the tip of the needle electrode for corona discharge 2. For this purpose, air is exhausted with a small pump from a joint for exhausting ion source unit 20, and its flow rate is at a level of several milliliters per minute to several liters per minute. Also, as depicted in FIG. 1, to prevent residence of water clusters from expiration between the counter electrode 5 and the detection electrode 6 and between the detection electrode 6 and the stop electrode 7, it is effective to exhaust air with a pump from a first exhaust-port joint 11 and a second exhaust-port joint 12 (its flow rate is at a level of several milliliters per minute to several liters per minute) or to cover this region not with a metal plate but with a mesh plate so that the region is made as an open system as much as possible. Still further, as depicted in FIG. 2, it is also important to provide, in addition to an expiration introduction port 14, an expiration discharge port 15 and a second expiration discharge port 16 in a sense to prevent residence of water clusters inside the monitor. Circles depicted in FIG. 2 each represent an ion-source exhaust port 13, a first expiration discharge port 18, and a second expiration discharge port 19. Here, since a high voltage is applied to the counter electrode 5, it is also important to provide a mesh plate for expiration introduction port 17a in view of prevention of an electric shock. A mesh plate for expiration discharge 17b is provided so as to prevent residence of water clusters from expiration inside the monitor.

From above, the current value to be detected by the present invention is thought to be simply represented by the following equation:

$$I = N \times e \times \alpha \times \beta.$$

Here, I (A): an amount of current to be detected by the detection electrode 6; N (pieces/s): the number of ions per unit time in a ion beam; e=electric charge (s·A) ; α (dimensionless): a ratio at which water clusters in expiration are charged; and β (dimensionless): a ratio at which generated cluster ions are detected by a monitor.

In general, partial pressures of expiration gas are said to be as follows: 566.0 mg (74.5%) of $N_2$, 120.0 mg (15.7%) of $O_2$, 27.0 mg (3.6%) of $CO_2$, and 47.0 mg (6.2%) of $H_2O$. In an atmosphere, normally, carbon dioxide is not contained and water vapor is less. However, when entering a respiratory tract, air is exposed to body fluid covering the surface of the respiratory tract, and air is completely moisturized before entering alveoli. Since the partial pressure of water vapor is 47 mm Hg at 37° C., this is a partial pressure of water vapor in alveolar gas. In these conditions, although depending on the environment (temperature and humidity), in consideration of human living space, water molecules are considered to become water clusters in expiration.

On the other hand, when expiration gas with the above-described composition is introduced to a positive corona discharge region, the following reaction is considered to occur:

$$N_2 + e = N_2^+ + 2e$$

$$N_2^+ + 2N_2 = N_4^+ + N_2$$

$$N_4^+ + H_2O = H_2O^+ + 2N_2$$

$$H_2O^+ + H_2O = H_3O^+ + OH$$

$$H^+(H_2O)_{n-1} + H_2O + N_2 = H^+(H_2O)_n + N_2$$

In general, as to $H_3O^+$, every time water molecules are hydrated, binding energy is added by $\Delta H_{n,n-1}$. Therefore, a proton affinity PA per water molecule is 169.3 kcal/mole, and PA increases as 201.3, 221.3, and 238.3, ... for two, three, and four molecules. Even PA for two water molecules has a large value of 201.3 kcal/mole, and water cluster ions practically cannot protonate most oxygen-containing organic compounds. Therefore, when expiration is ionized by corona discharge, ions to be generated are considered to be substantially an aggregate of water cluster ions. A characteristic reaction shown by water ion clusters is the following substitution reaction:

$$H^+(H_2O)_n + A = A^+(H_2O)_{n-1}B = H_2O.$$

Here, A is a molecule other than water. This substitution reaction generally occurs early and often occurs with a collision velocity. Also, since heat of reaction is carried away as translational energy, the reaction can be said as an extremely soft ion-molecule reaction.

Figure 3:
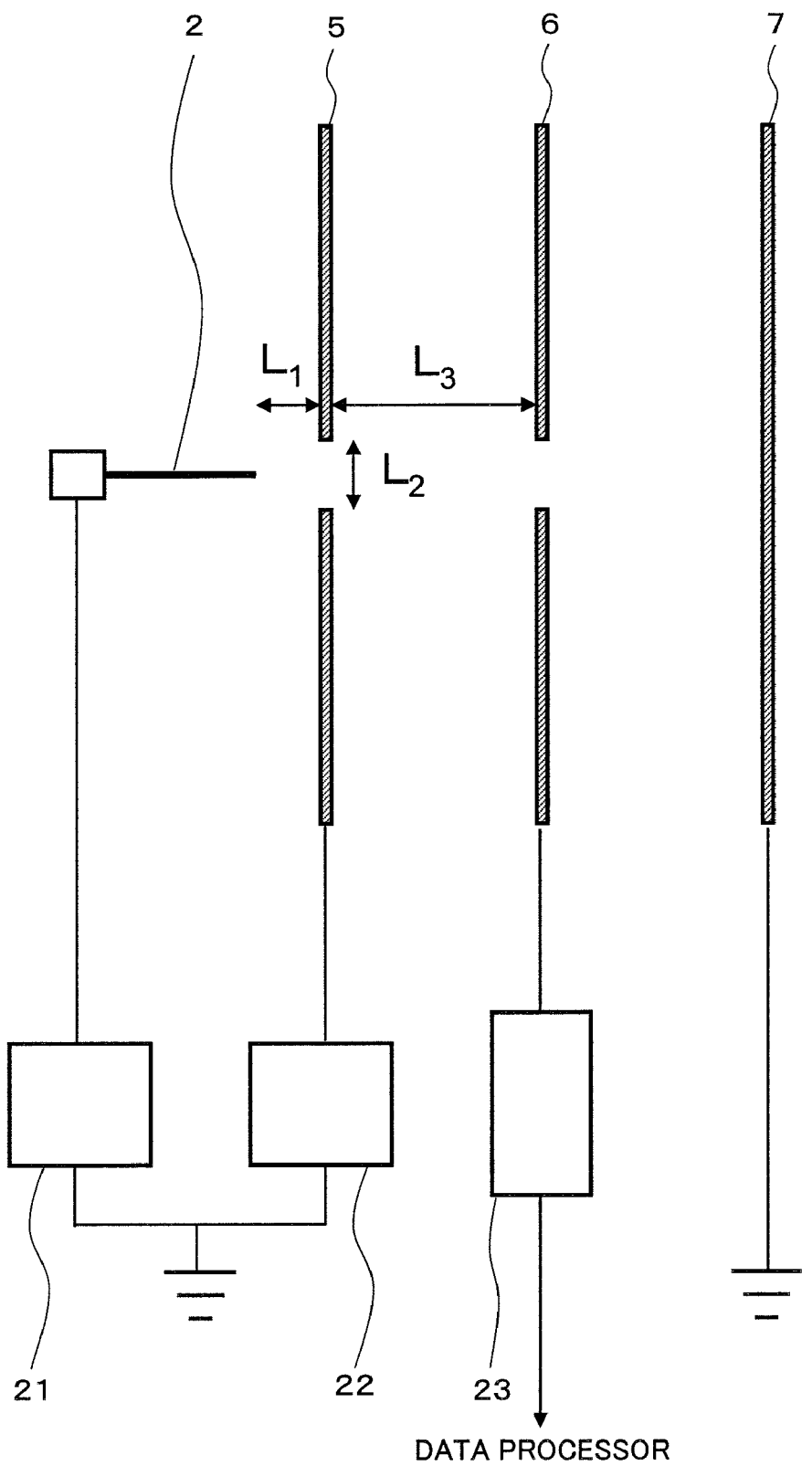
FIG. 3 is a structural diagram of electrodes and a power supply in the device of the present invention.

In FIG. 3, when a distance $L_1$ between the needle electrode for corona discharge 2 and the counter electrode 5=3 mm, an opening diameter $L_2$ of the counter electrode 5=3 mm, and a distance $L_3$ between the counter electrode and the detection electrode=10 mm, an amount of current due to water cluster ions to be detected with $5 \times 10^{-4}$ m³/second, which can be regarded as an amount for one air change, is approximately 1 μA when introduction is made near the ion beam region and the corona discharge current is 4 μA. Therefore, α can be estimated as follows:

$$\alpha \approx 0.25.$$

Figure 4:
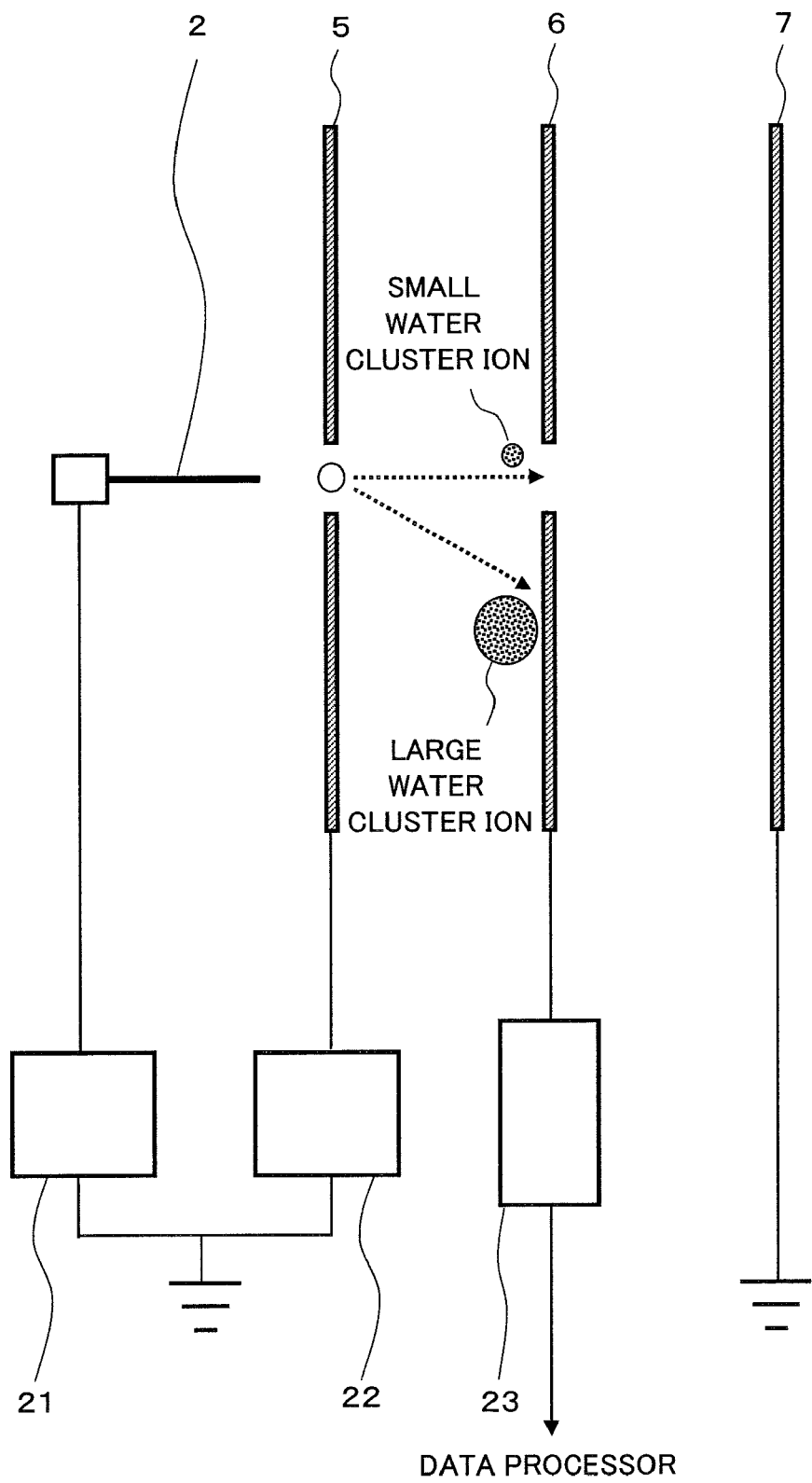
FIG. 4 is a diagram of the principles in the device of the present invention.

Briefly in summary, with the water clusters in expiration reacting with the ion beam generated by corona discharge and part of the ion beam proceeding straight ahead resultantly being deflected in the direction of the force of gravitation, the water clusters in expiration are detected (FIG. 4).

To analyze the course of this process, it is required to analyze a motion of the water cluster ions in the direction of the force of gravitation and a motion thereof in a direction at right angles to the force of gravitation. First, the motion of the water cluster ions in the direction of the force of gravitation is analyzed. Air resistance acting on small clusters is found by Stokes to be proportional to a radius r of a sphere and a velocity $v_g$ of the sphere in the direction of the force of gravitation. The magnitude of air resistance is represented by the following equation with the use of a coefficient of viscosity of air η:

$$\text{Magnitude of air resistance}=6\pi\eta r v_g.$$

Also, since the magnitude of a buoyant force by air is equal to a force of gravitation acting on air displaced by the object, in the case of a sphere having a radius r, by using a density of air $\rho_f$ and acceleration due to gravity g, the magnitude is represented as follows:

$$\text{Magnitude of the buoyant force by air}=(4/3)\pi r^3\rho_g g.$$

Therefore, an equation of motion when water clusters each having mass m acting in the direction of the force of gravitation is represented as:

$$m \cdot (dv_g/dt) = (4/3)\pi r^3 \rho_p g - 6\pi \eta r v_g - (4/3)\pi r^3 \rho_f g.$$

Here, $\rho_f$ is a density of water. Considering droplets falling in the air at 1 atmospheric pressure and 25° C., the density of water $\rho_p$=997.04 kg/m³, the density of air $\rho_f$=1.1843 kg/m³, the coefficient of viscosity of air η=0.0000182 (25° C.), and the acceleration due to gravity g=9.807 m/s². When $v_g$ is positive, the acceleration becomes 0 as time passes, and the water clusters in the air begins a uniform motion at a constant velocity. A terminal velocity $v_{g0}$ of this velocity is represented by the following equation with the above equation being set as zero.

$$V_{g0} = 2r^2(\rho_p - \rho_f)g/(9\eta)$$

Next, the motion of the water cluster ions at right angles to the direction of the force of gravitation is described. With the electric charge of the water cluster ions being assumed to be q, when the magnitude of the electric field is E, an equation of motion in the case of the motion at right angles to the direction of the force of gravitation for the water cluster ions is as follows.

$$m \cdot (dv_t/dt) = qE - 6\pi \eta r v_t$$

Therefore, a terminal velocity $V_{t0}$ at this time is $$v_{t0} = qE/(6\pi \eta r).$$

Here, the electric charge q=1.6021×10⁻¹⁹ C(A·s). For example, if 350 V is applied to a distance of 10 mm between an electrode for leading and an electrode for detection, the electric field E=35000 V/m.

Figure 5:
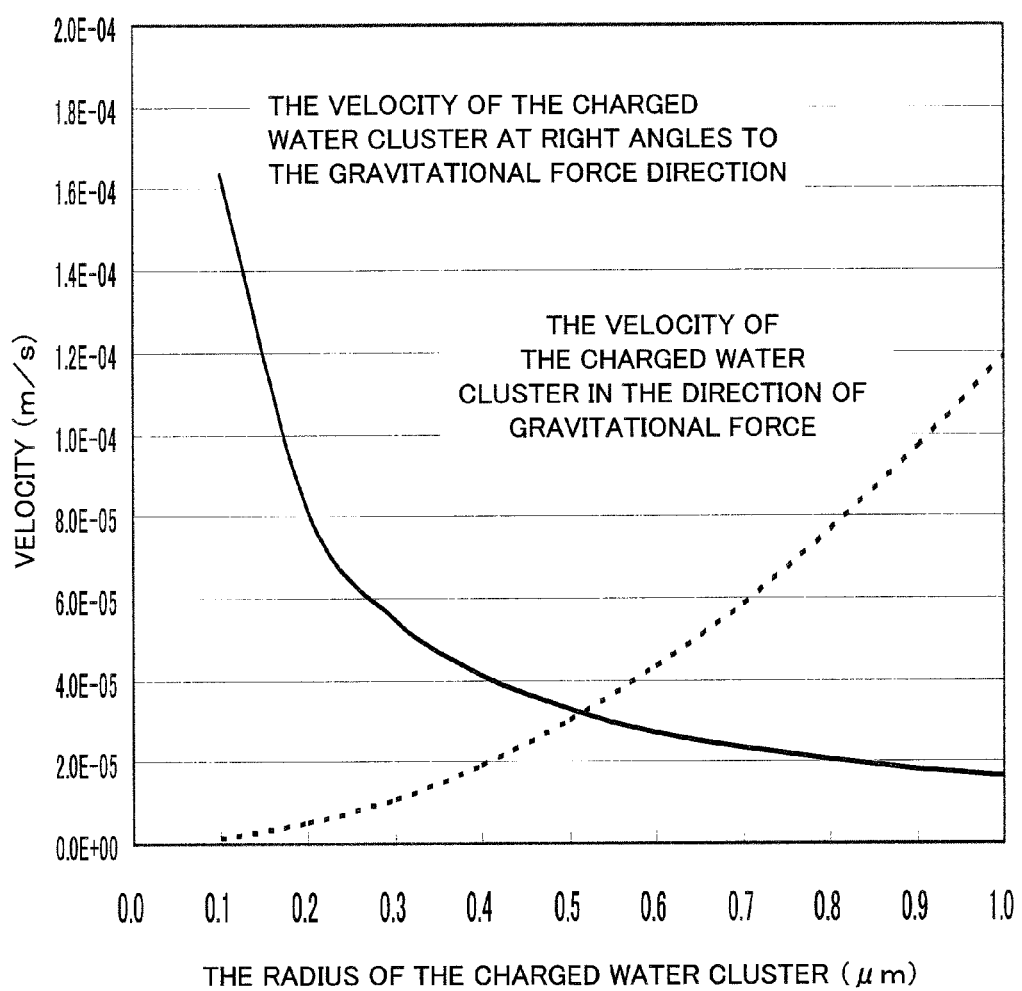
FIG. 5 depicts calculated values of a velocity in a direction of the force of gravitation and a velocity in an electric field direction at right angles to the direction of the force of gravitation depending on the radius of a water cluster ion in the device of the present invention.
Figure 6:
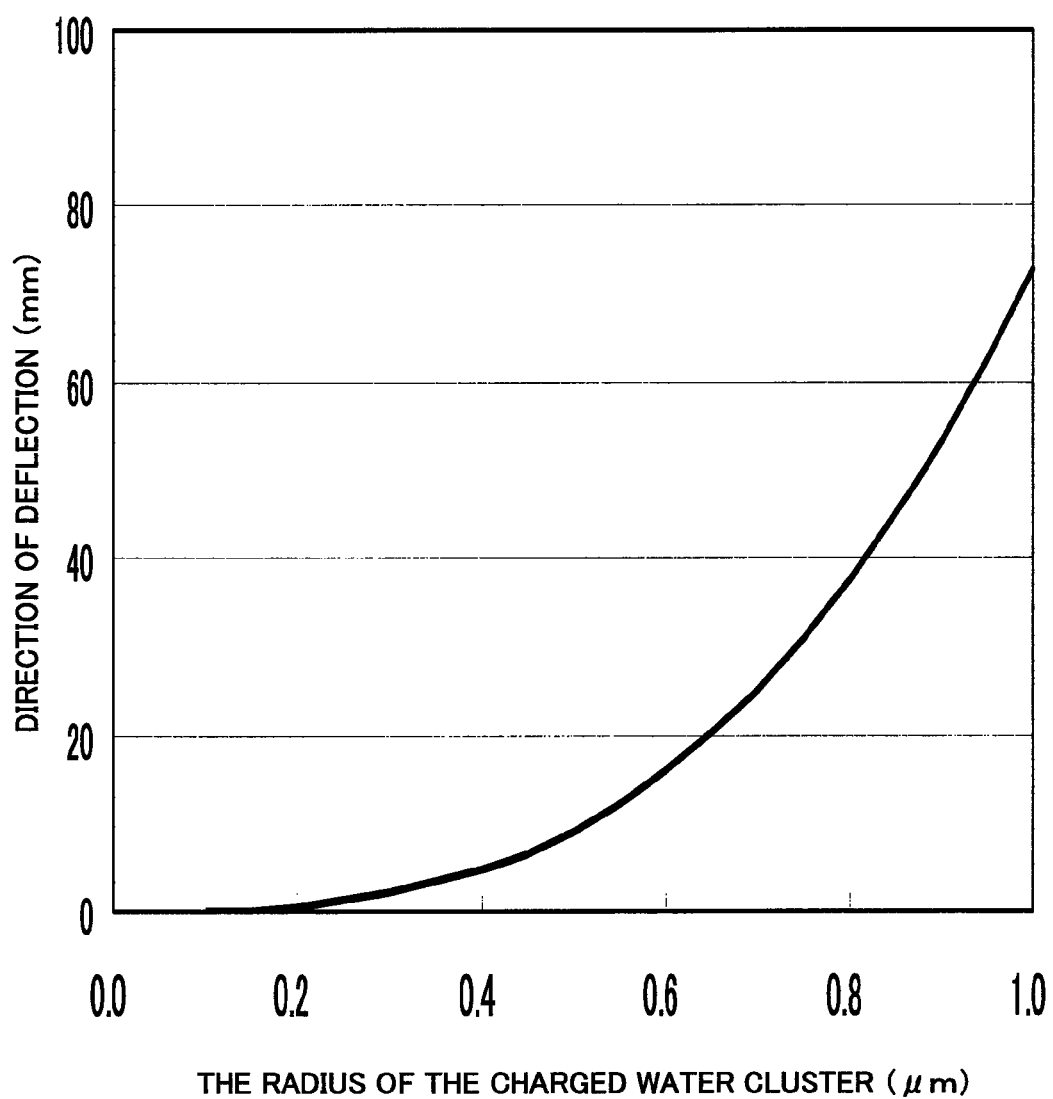
FIG. 6 depicts calculated values of a deflection distance depending on the radius of a water cluster ion in the device of the present invention.

Here, assume the case of water clusters at 1 atmospheric pressure and 25° C. in the air. With the density of water $\rho_p$=997.04 kg/m³, the density of air $\rho_f$=1.1843 kg/m³, the coefficient of viscosity of air η (25° C.)=0.0000182, the acceleration due to gravity g=9.807 m/s², the electric charge q=1.6021×10⁻¹⁹ C(A·s), and the electric field E=35000 V/m, changes of $v_{g0}$ and $V_{t0}$ with the radius of each water cluster are calculated as depicted in FIG. 5. For example, when the distance $L_1$ between the needle electrode for corona discharge 2 and the counter electrode 5=3 mm, the opening diameter $L_2$ of the counter electrode 5=3 mm, and the distance $L_3$ between the counter electrode and the detection electrode=10 mm in FIG. 3, for water cluster ions generated from the center of the counter electrode 5 to collide with the detection electrode 6, an amount of deflection of at least 1.5 mm is required. Here, the radius of the water cluster ion is estimated to be 0.27 μm (refer to FIG. 6).

Now consider the case in which 2.5×10¹² water cluster ions each having an electric charge of 1.6021×10⁻¹⁹ C and a radius of 0.1 μm are generated per second from the opening of the counter electrode 5. While the water cluster ions initially generated are drifting between the counter electrode 5 and the detection electrode 6, when coupling with water clusters occurs a plurality of times, the radius of the water cluster ion is increased with the entire electric charge being kept. For example, when about forty three water cluster ions each having a radius of 0.1 μm are coupled, the radius is increased to 0.35 μm, and the amount of deflection becomes approximately 3.1 mm. In this case, with an enormous increase of water cluster ions due to the reaction of the water cluster ions and the water clusters, almost all of the initial water cluster ions each having the radius of 0.1 μm can be detected. As a result, a current at a μA level is detected.

Figure 7:
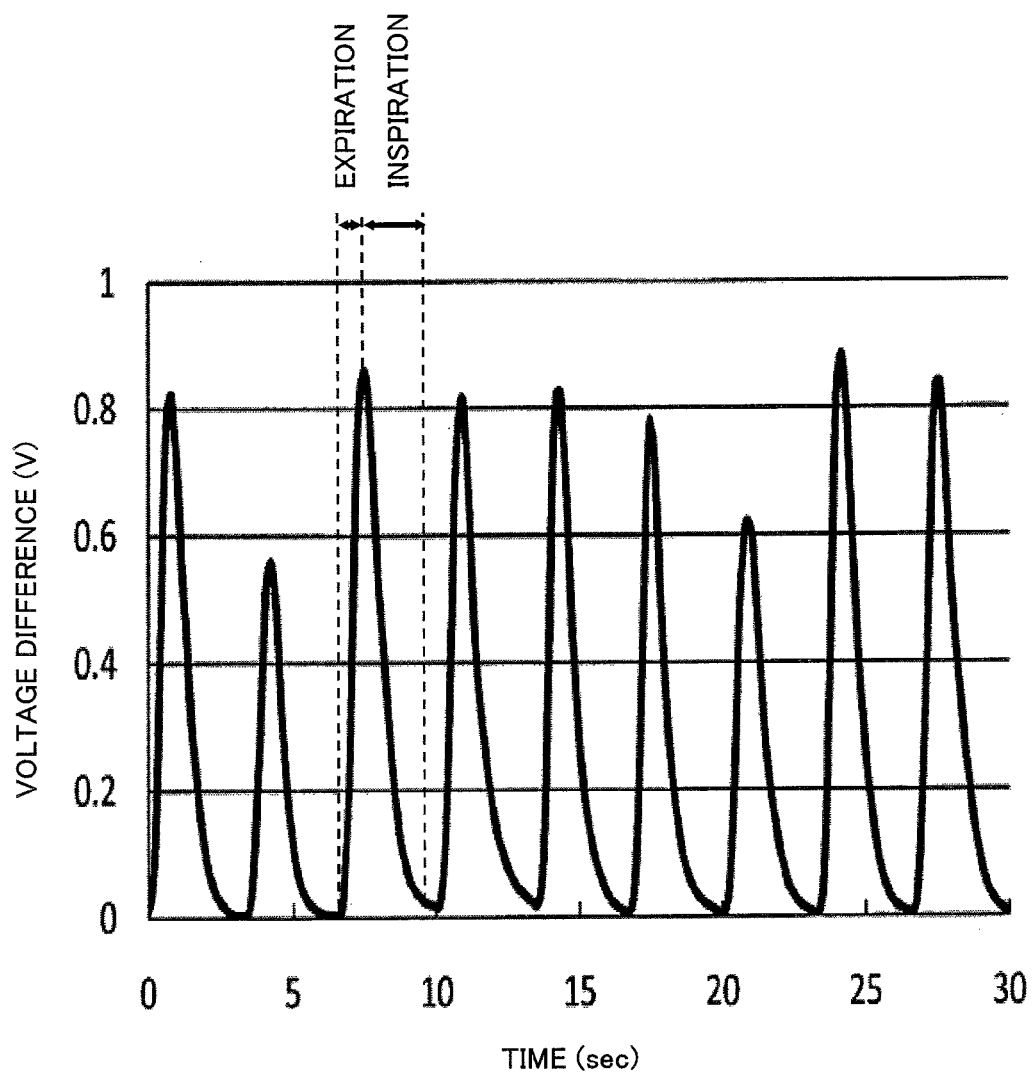
FIG. 7 depicts an example of expiration detection in the device of the present invention.
Figure 8:
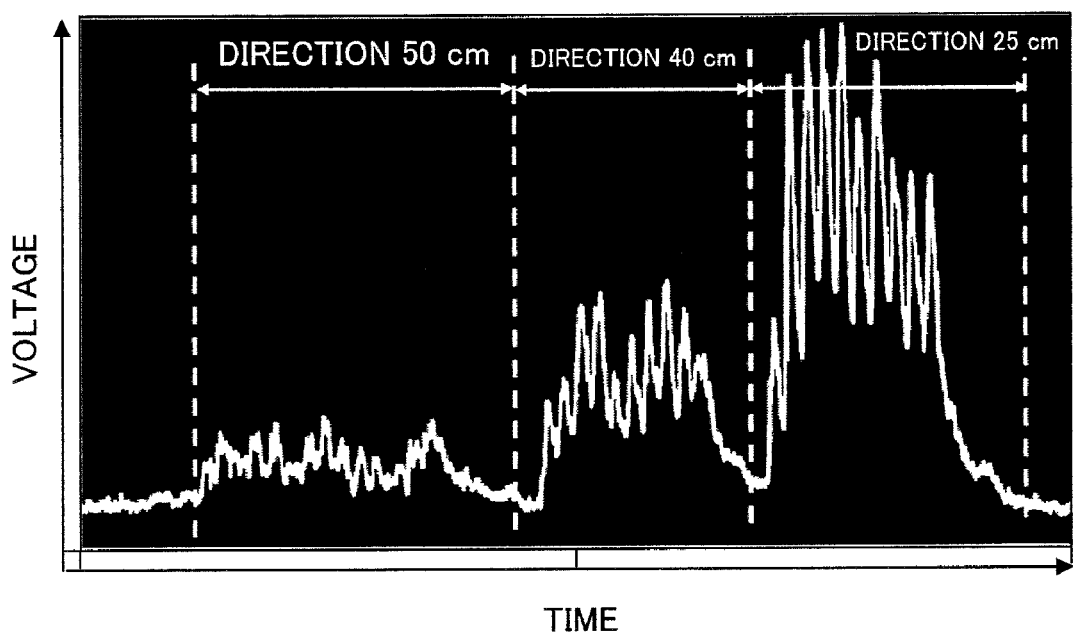
FIG. 8 depicts distance dependency of expiration detection in the device of the present invention.
Figure 9A:
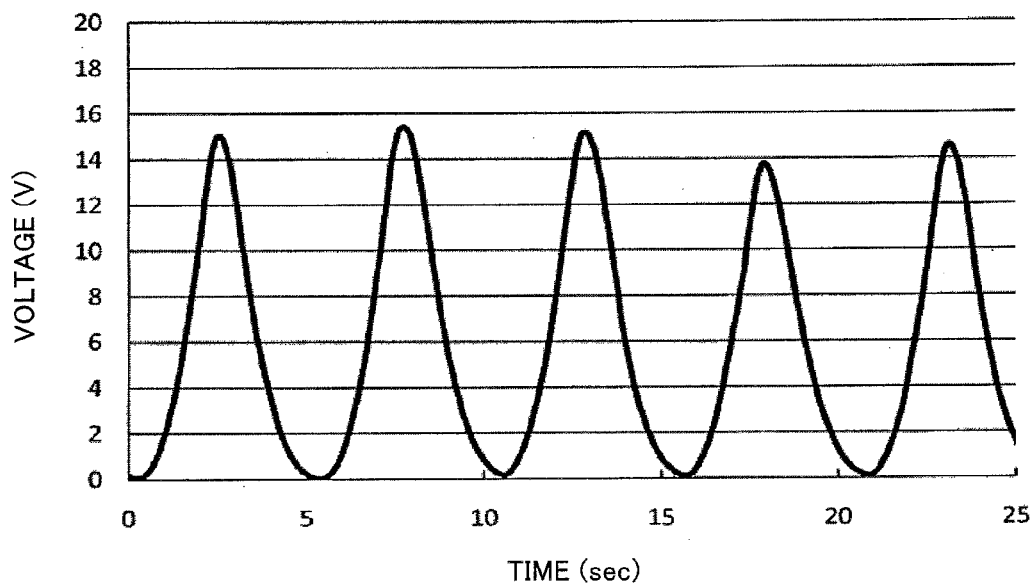
FIGS. 9A and 9B depict humidity dependency in the air in the device of the present invention.
Figure 9B:
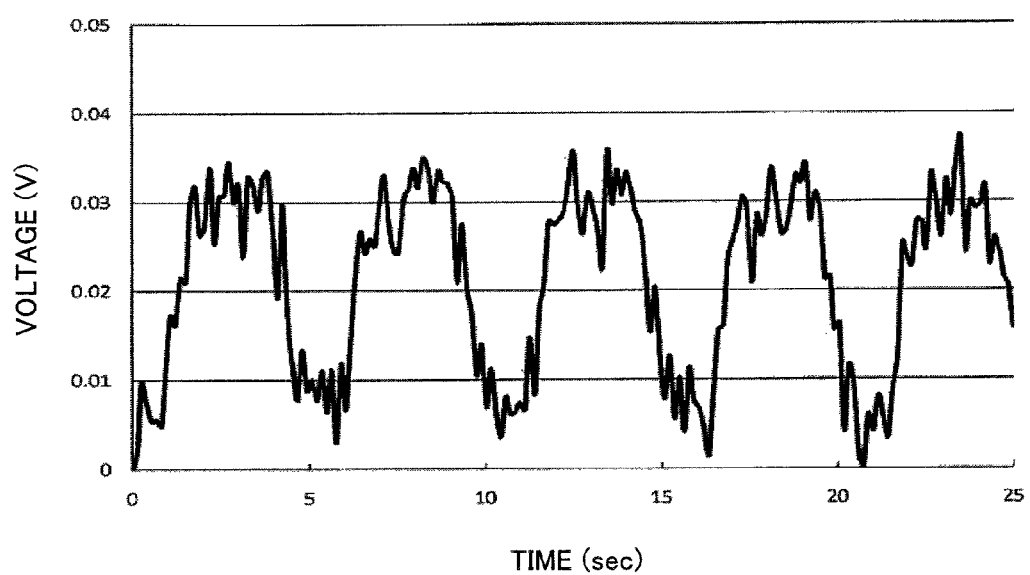

FIG. 7 depicts an example of expiration detection in a non-contact manner when the present invention is used. It is confirmed that one cycle with expiration and inspiration is detected as one peak (hereinafter referred to as an expiration peak). This is data when the distance between the mouth of the test subject and the expiration introduction port 14 is on the order of 15 cm. Distance dependency between the mouth of the test subject and the expiration introduction port 14 is depicted in FIG. 8. Even the distance is 50 cm apart, the expiration peak is clearly detected, and a high performance regarding the non-contact property of the present technique can be found. Also, in the present invention, to indicate that the water clusters are a main cause for changes in the amount of current in the detection electrode 6, a difference occurring when an airflow with a humidity on the order of 30% and an airflow with a humidity on the order of 18% are repeatedly generated for detection by using a syringe containing water and a syringe without containing water is depicted in FIGS. 9A and 9B. It is found that the signal strength in the case of the humidity on the order of 30% is about 500 times stronger, and this shows strong involvement by water clusters in expiration in the detection technique of the present invention.

While the case of positive ions generated by using positive corona discharge is described in the example above, it goes without saying that negative ions generated by using negative corona discharge can be used.

Figure 10A:
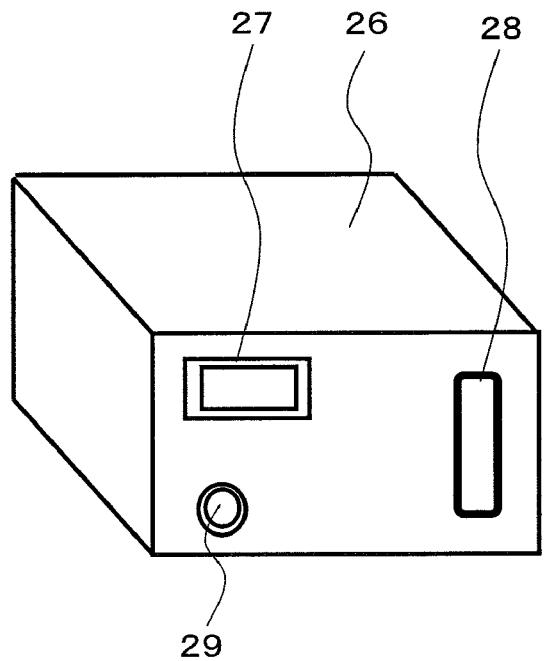
FIGS. 10A and 10B depict a sensor box having the device of the present invention accommodated therein.
Figure 10B:
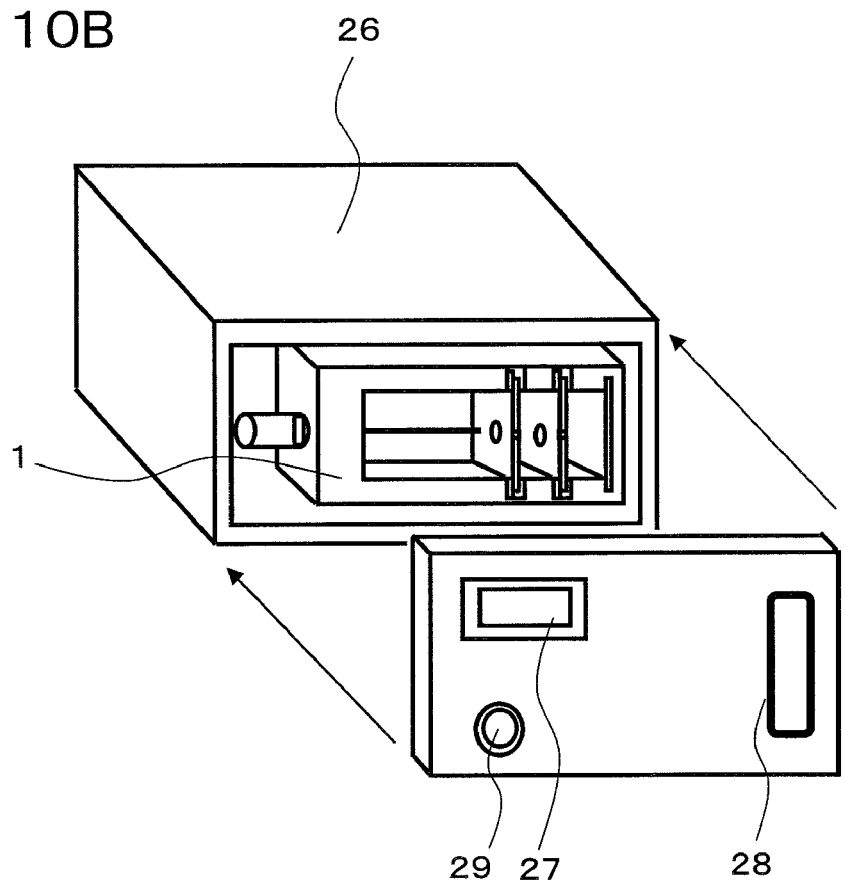

FIGS. 10A and 10B depict a sensor box 26 having the sensor unit 1 using alcohol detection incorporated therein. Expiration is introduced from a sensor-box expiration introduction port 29, and the results are displayed on a display 27 with lights varied in numerical values or colors. A switch 29 is for turning on the power supply of this sensor box.

Second Embodiment

Figure 11A:
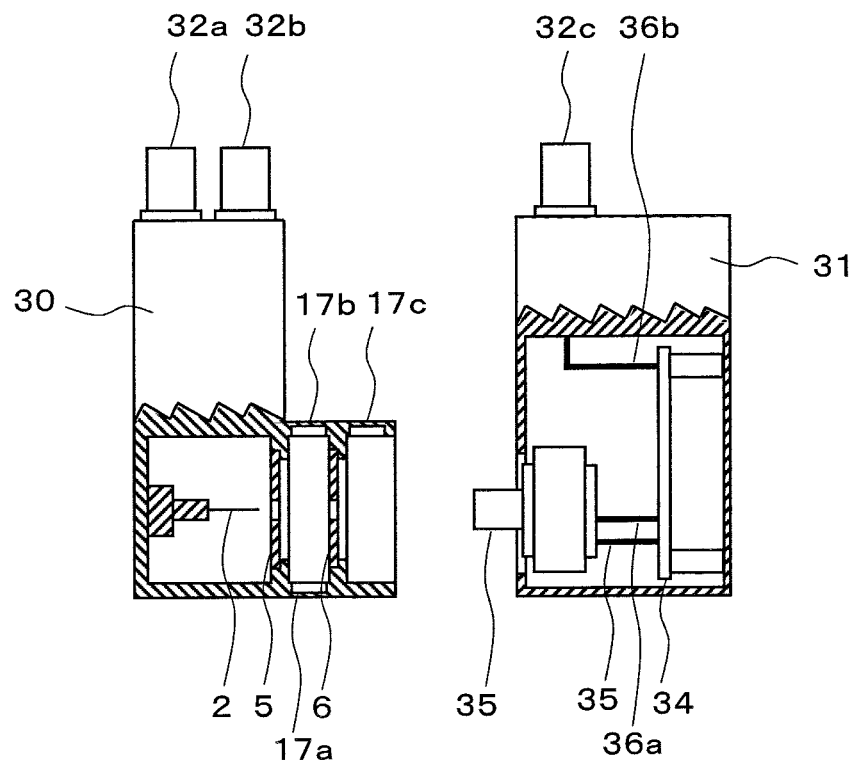
FIGS. 11A and 11B depict an example in which an alcohol sensor is disposed in the present invention.
Figure 11B:
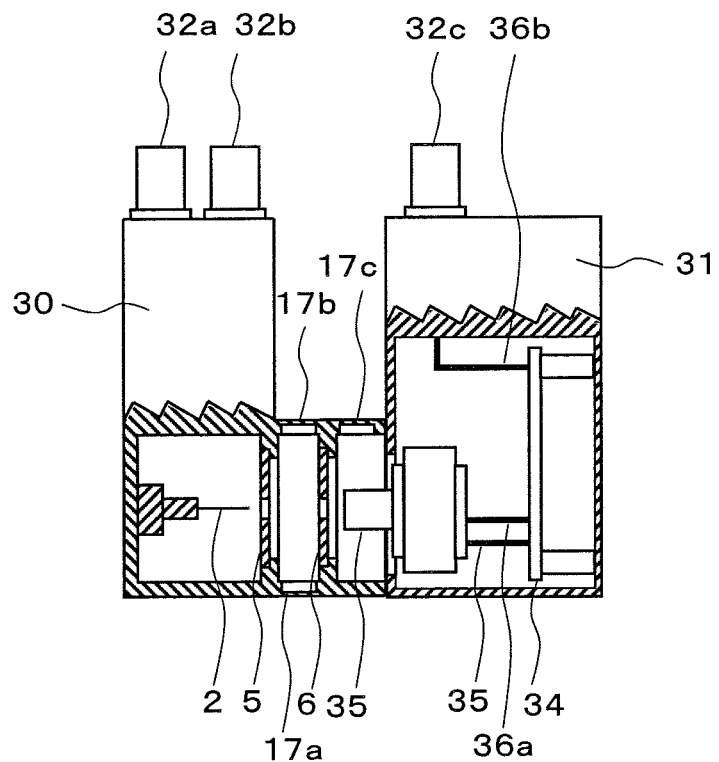

The present invention can be used for a preventive device for drink-driving. Examples of the case in which the present invention is used for an automobile are depicted in FIGS. 11A and 11B. FIG. 11A depicts the case in which an expiration monitor unit 30 and an alcohol sensor unit 31 are dividedly provided, and FIG. 11A depicts the case in which the expiration monitor unit 30 has the alcohol sensor unit 31 incorporated therein. In the expiration monitor unit 30, the needle electrode for corona discharge 2, the counter electrode 5 having an opening, the detection electrode 6 also having an opening, the mesh plate for expiration introduction port 17a, and mesh plates for expiration discharge port 17b and 17c. To the needle electrode for corona discharge 2 and the counter electrode 5, a voltage is applied through connectors 32a and 32b. Normally, a voltage from several hundreds of volts to several kV is applied to the needle electrode for corona discharge 2 (a voltage from several hundreds of volts to several kV is applied between the needle electrode for corona discharge 2 and the counter electrode 5 by using a constant-current high-voltage power supply to obtain a current of several μA), and a voltage of several hundreds of volts is applied to the counter electrode (the voltage is on the order of 50 to 600 volts when the distance between the counter electrode 5 and the detection electrode is 10 mm). On the other hand, in the alcohol sensor unit 31, an alcohol sensor head 33 such as a semiconductor sensor, a sensor control board 34, a sensor control line 35, a signal line 36a, an output signal line 36b, and a connector 32c are provided. As the alcohol sensor head 33, not a semiconductor sensor but a sensor of another type such as a fuel cell type can also be used.

Figure 12:
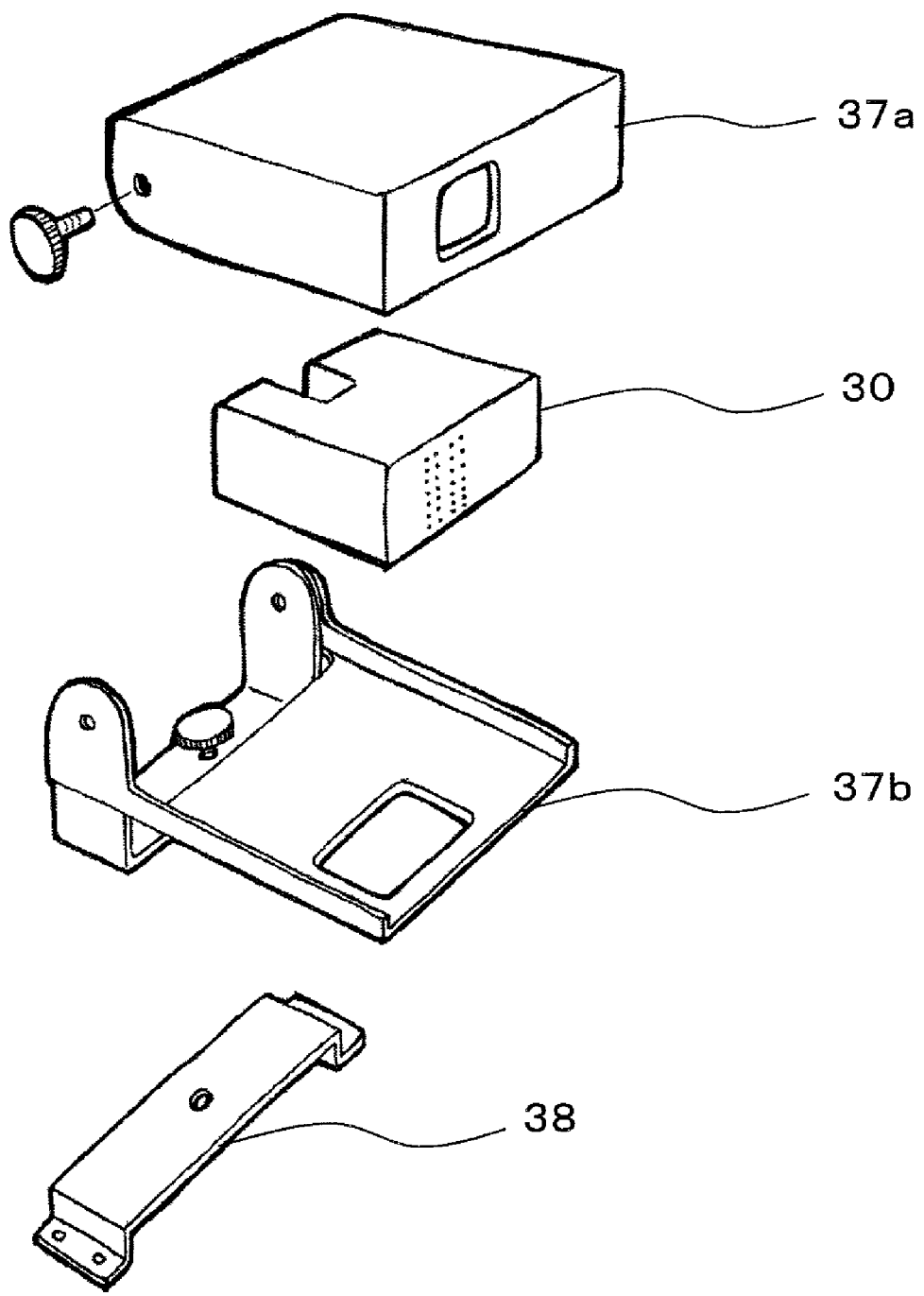
FIG. 12 is an example in which an expiration detecting unit and an alcohol sensor unit are cased.
Figure 13:
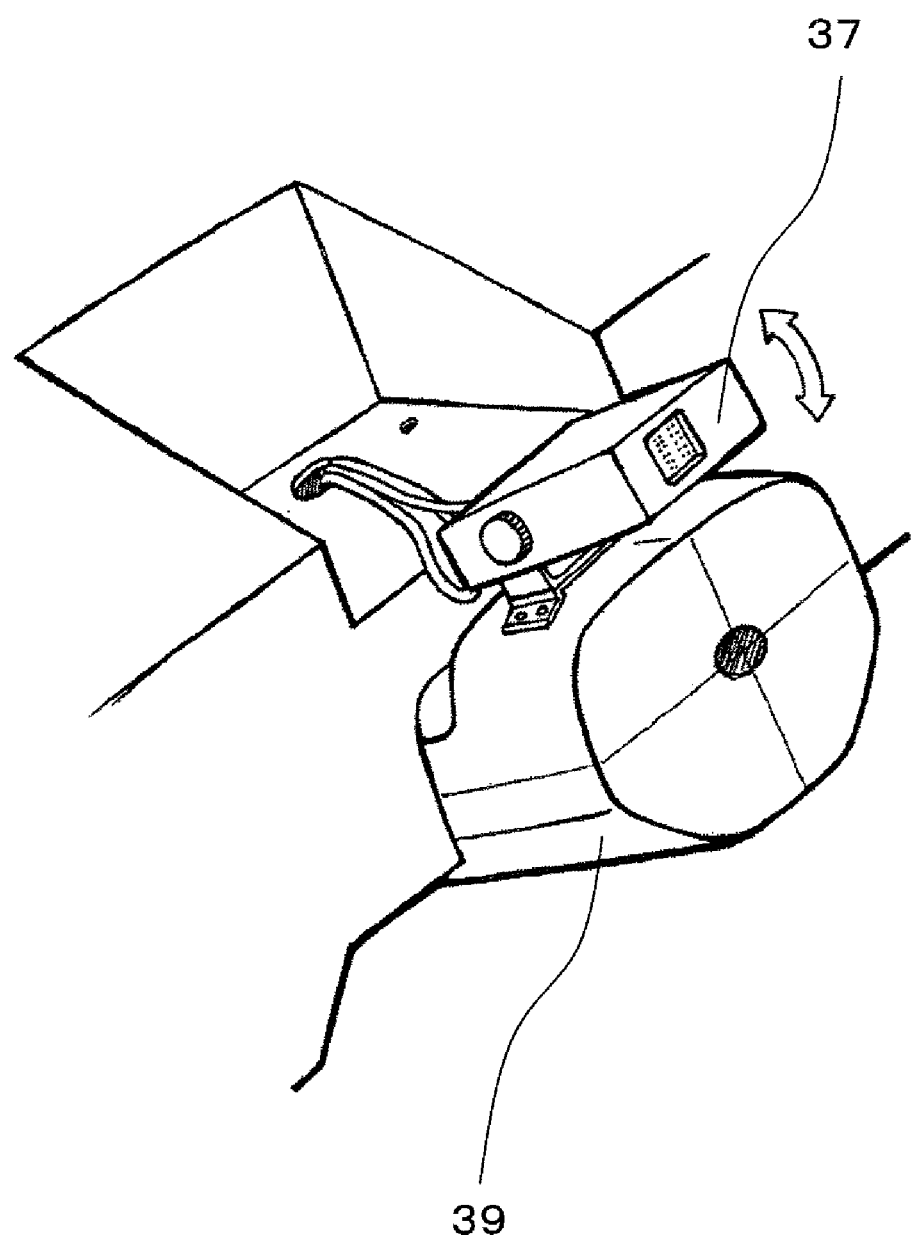
FIG. 13 depicts an example in which the expiration detecting unit and the alcohol sensor unit are installed onto a column.

FIG. 12 depicts the case in which the expiration monitor unit 30 and the alcohol sensor unit 31 are accommodated in monitor cases 37a and 37b. This monitor case 37 is installed onto a column cover 39 via a base 38 as depicted in FIG. 13.

Figure 14A:
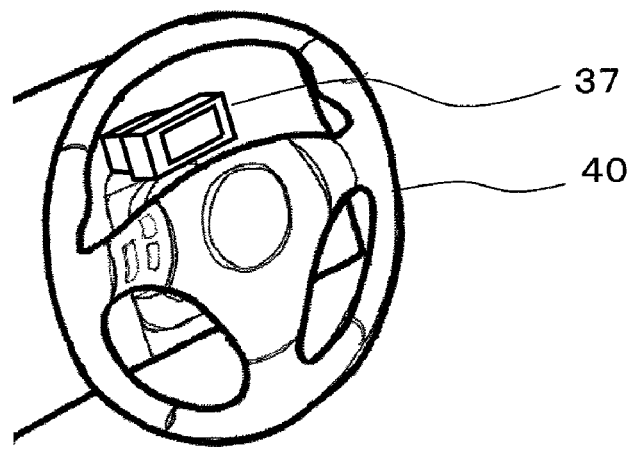
FIGS. 14A and 14B are diagrams of the principles of alcohol check on a driver in the present invention.
Figure 14B:
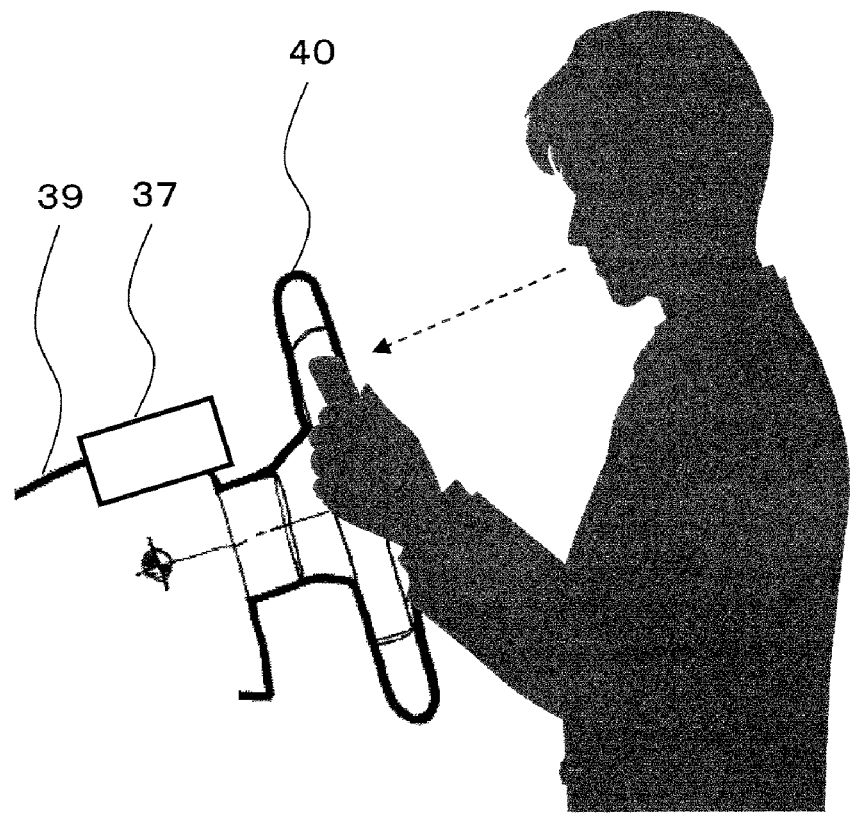

On the base 38, it is important to make an angle of the monitor case 37 with respect to the driver variable. One installation place of the monitor case 37 is on the column cover 39 behind a steering wheel 40 depicted in FIG. 14A. In this case, as depicted in FIG. 14B, expiration of the driver reaches the monitor case 37 from a gap in an upper half of the steering wheel 40. Therefore, in addition to the example depicted in FIGS. 14A and 14B, the case can be attached onto a dashboard beside the steering wheel. With the sensor box disposed at this position, the chances of disguise by a passenger (a passenger free of alcohol takes an alcohol test in place of the driver) can be significantly reduced. In particular, it is effective to dispose the sensor box on the dashboard on a window side. However, when the sensor box is attached onto the dashboard beside the steering wheel, an alcohol test at the time of engine start is mainly performed.

Figure 15:
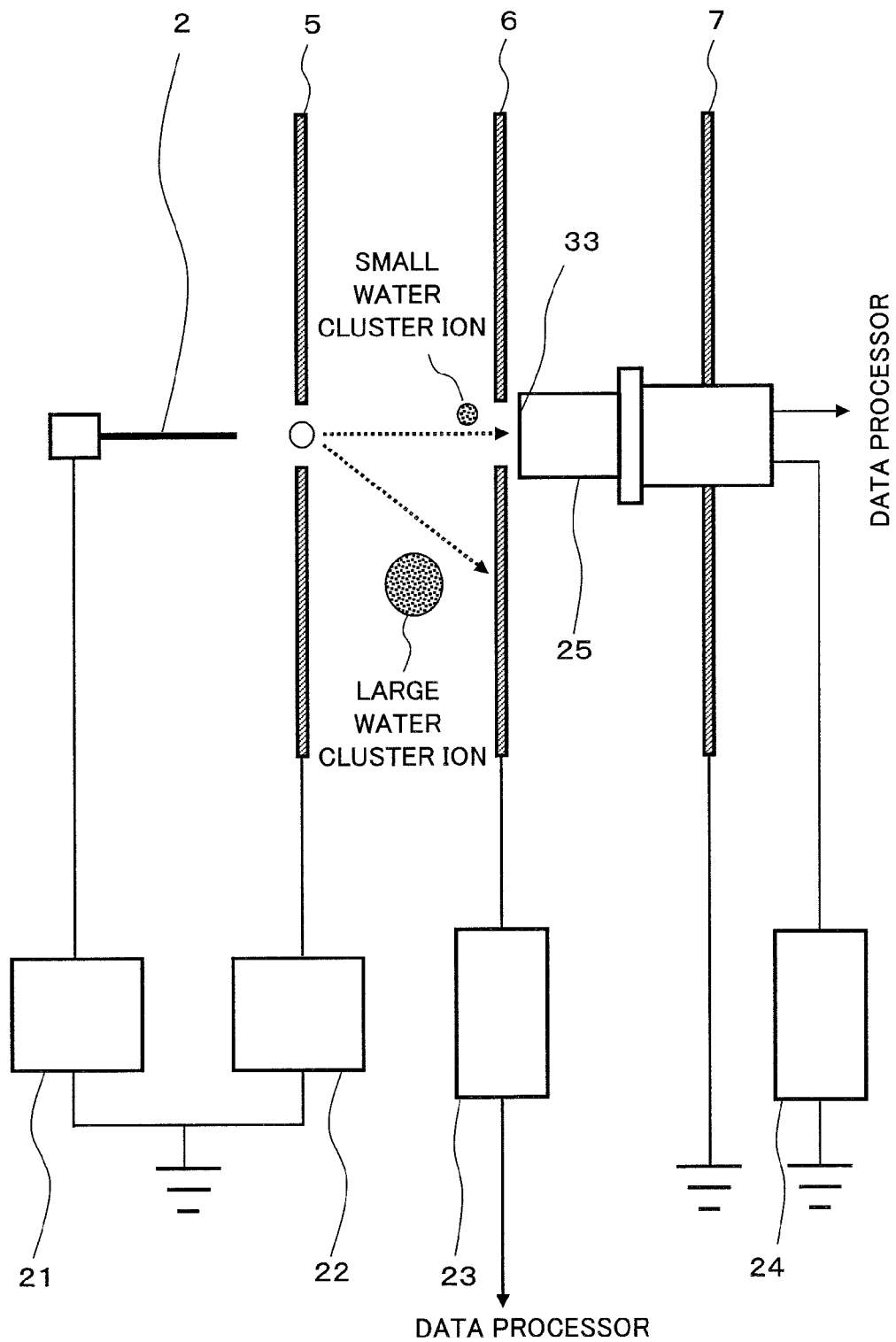
FIG. 15 is a diagram depicting a position of an alcohol sensor head on an axis of a needle electrode for corona discharge in the present invention.

FIG. 15 depicts an example of electrode structure inside the expiration monitor unit. An ion beam occurring between the needle electrode for corona discharge 2 and the counter electrode 5 is accelerated by a voltage applied between the counter electrode 5 and the detection electrode 6 in a direction of the detection electrode. Here, when expiration is introduced from a direction perpendicular to the paper surface of FIG. 15 toward the paper surface for several seconds, water clusters from expiration react with ions, and the ion beam with its weight increased is deflected in the direction of the force of gravitation as depicted in FIG. 15 to collide with the detection electrode 6 to be detected as a current. Here, as depicted in FIG. 15, when the alcohol sensor head 33 is disposed on a line extending from the needle electrode for corona discharge 2, part of alcohol contained in expiration is detected. In this case, however, a large amount of ions generated from the corona-discharge-purpose electrode 2 are always introduced to the alcohol sensor head 33, the alcohol sensor head 33 may be damaged. To get around this, as depicted in FIG. 16, if the alcohol sensor head 33 is shifted from the line extending from the needle electrode for corona discharge 2 by approximately 1 mm to 20 mm (when the distance between the counter electrode 5 and the detection electrode 6 is on the order of 10 mm), part of the ion beam from the needle electrode for corona discharge 2 is introduced to the alcohol sensor head 33 only when expiration is introduced, which is convenient in view of enhancement of longevity of the alcohol sensor.

Figure 16:
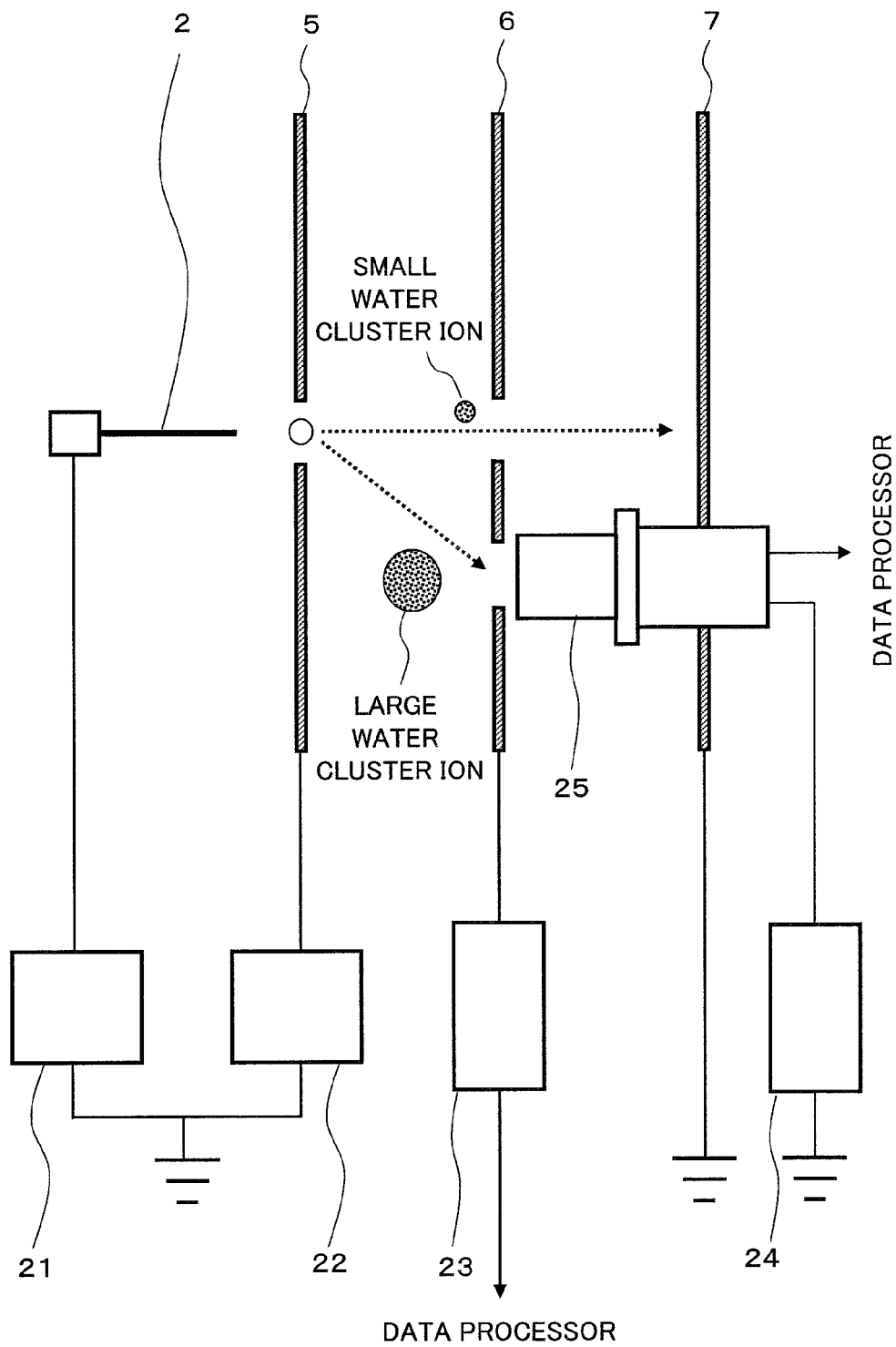
FIG. 16 is a diagram depicting a position of the alcohol sensor head with an axis shifted from the needle electrode for corona discharge in the present invention.
Figure 17A:
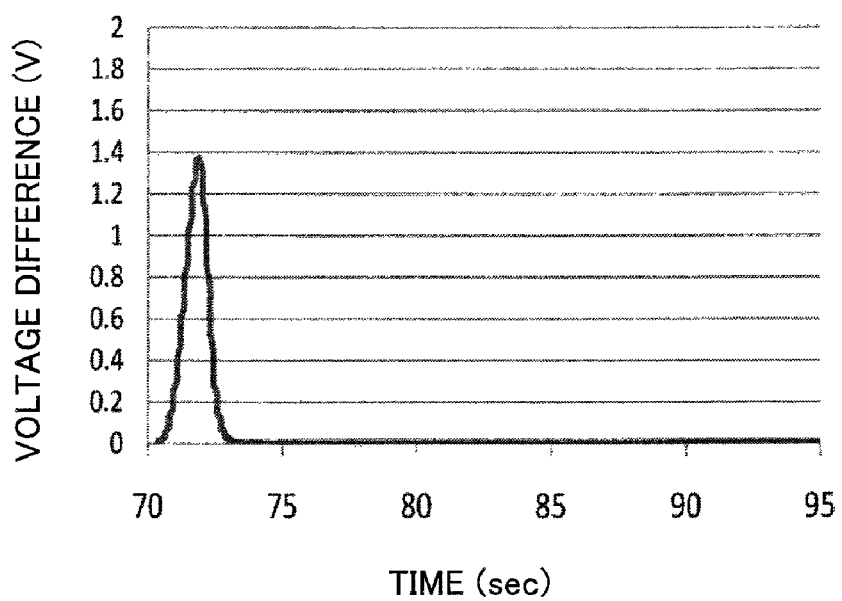
FIGS. 17A and 17B depict an example of simultaneous detection of expiration and alcohol when the alcohol sensor head with the axis shifted from the needle electrode for corona discharge is used in the present invention.
Figure 17B:
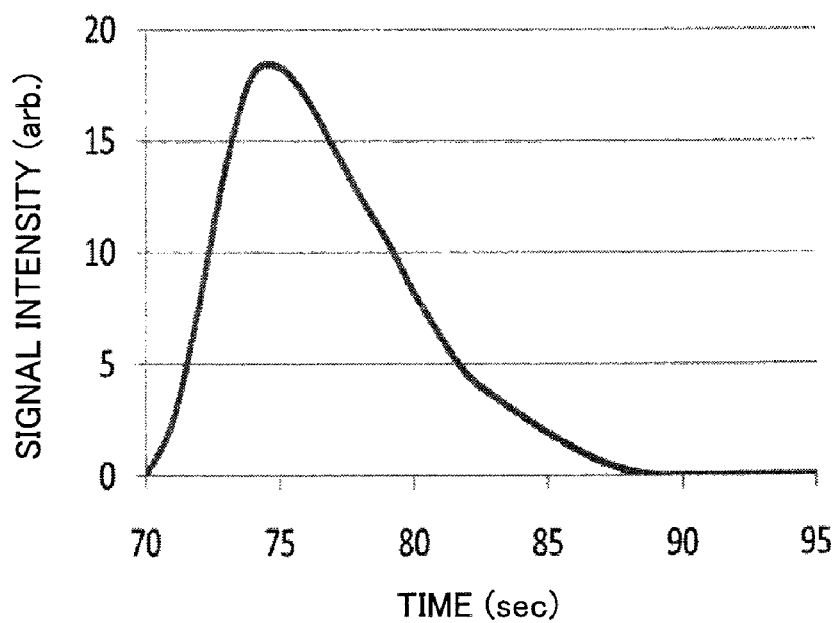
Figure 33A:
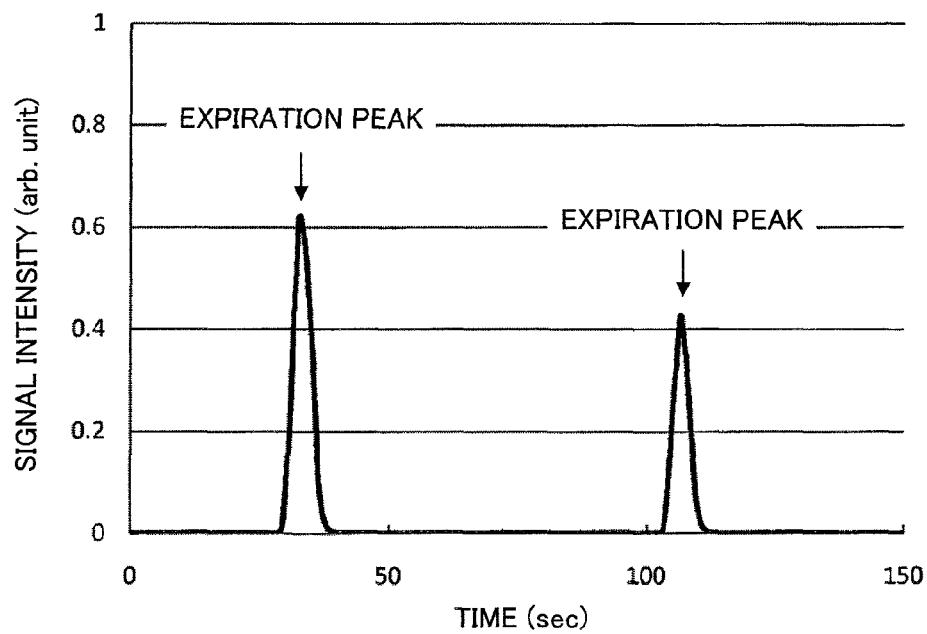
FIGS. 33A and 33B depict an example of alcohol detection in the present invention.
Figure 33B:
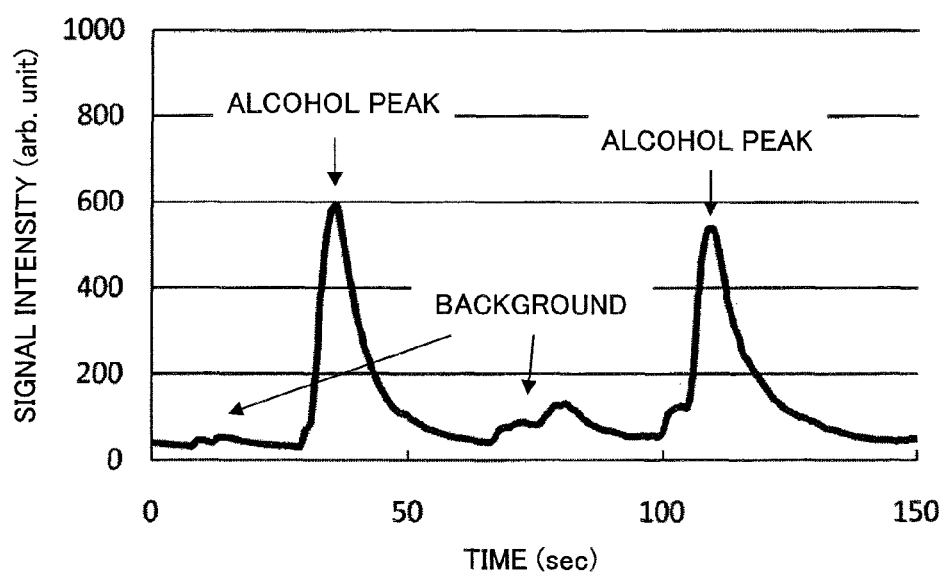

FIGS. 17A and 17B depict an example of an expiration peak and an alcohol peak in conjunction therewith detected when the structure of FIG. 16 is used. As such, detecting an expiration peak and then detecting an alcohol peak is an important index for showing that alcohol in expiration is detected, instead of showing that merely alcohol (ethanol) is detected. By using this characteristic, even if a passenger drinks alcohol and exhales alcohol (ethanol) inside the vehicle, a background due to alcohol (ethanol) derived from exhalation can be distinguished. FIGS. 33A and 33B depicts an example of the case in which the driver and a passenger are both drunken (as a matter of course, however, the vehicle is not in a driving state at this time). FIG. 33A is an example of detection of expiration peaks of a person in a driver's seat, and FIG. 33B is an example of detection of backgrounds by expiration of a passenger and alcohol peaks in conjunction with expiration of the person in the driver's seat. As depicted in FIG. 33B, even when the backgrounds due to expiration alcohol from the drunken passenger are being observed, with the alcohol peaks in conjunction with expiration of the person in the driver's seat being detected, it can be easily found that the person in the driver's seat is drunken.

Figure 18A:
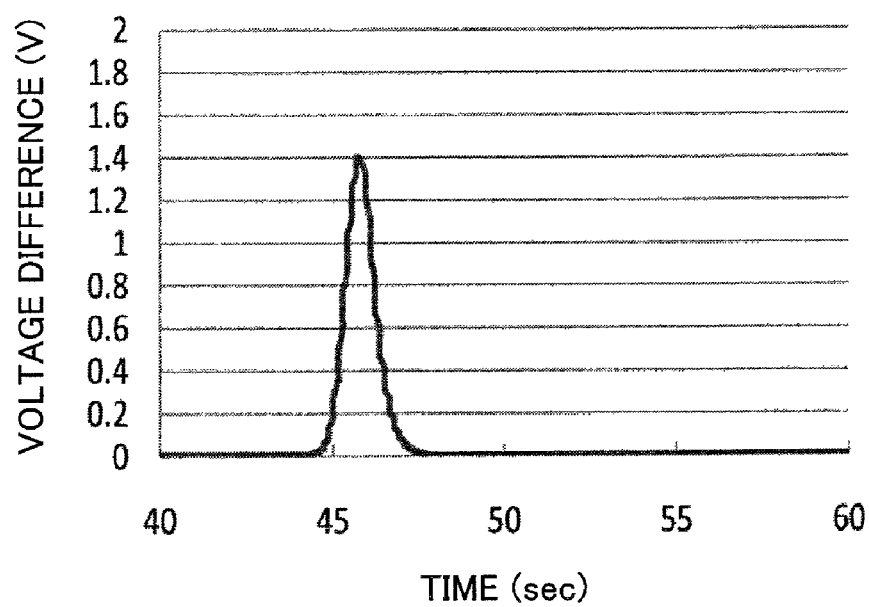
FIGS. 18A and 18B depict an example of simultaneous detection of expiration and alcohol when the axis of the alcohol sensor head is on the axis of the needle electrode for corona discharge in the present invention.
Figure 18B:
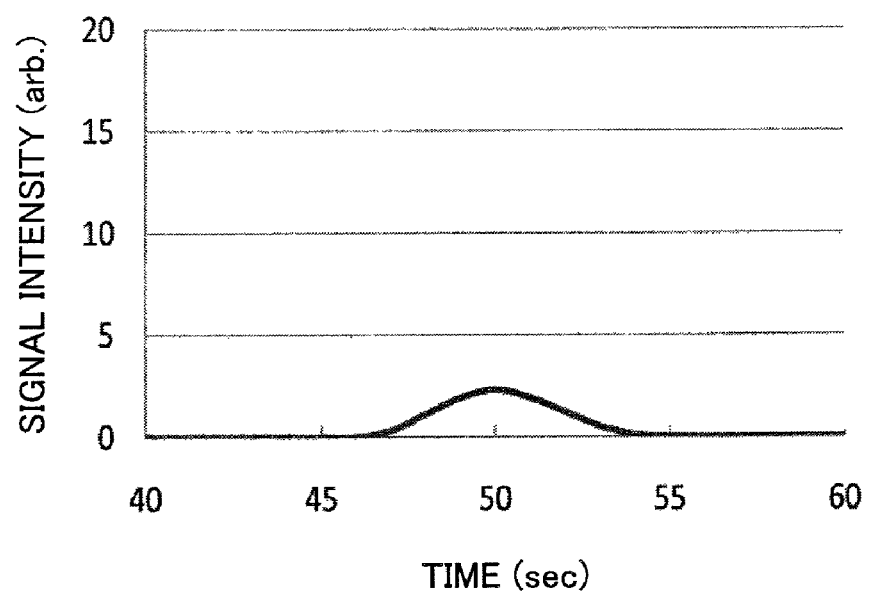

In FIGS. 17A and 17B, a peak top of the expiration peak and a peak top of the alcohol peak are slightly shifted in position from each other. This is a matter of where the alcohol sensor head 33 is disposed, and whether both timings match each other can be determined in consideration with this time difference. In addition, a shift of the position of the alcohol sensor head 33 from the line extending from the needle electrode for corona discharge 2 also has an influence on alcohol detection sensitivity. FIGS. 18A and 18B depict an expiration peak and an alcohol peak on the same condition as that of FIGS. 17A and 17B (expiration measurement after two hours from the time when 180 ml of wine with a concentration of alcohol of 11% is taken). The alcohol peak in FIGS. 18A and 18B is lower than the alcohol peak in FIGS. 17A and 17B. This is because many alcohol molecules in expiration are present in water clusters. Incidentally, in the case of FIGS. 18A and 18B, the axis of the needle electrode for corona discharge 2 and the axis of the alcohol sensor head 33 are shifted from each other by approximately 6 mm herein.

Figure 19:
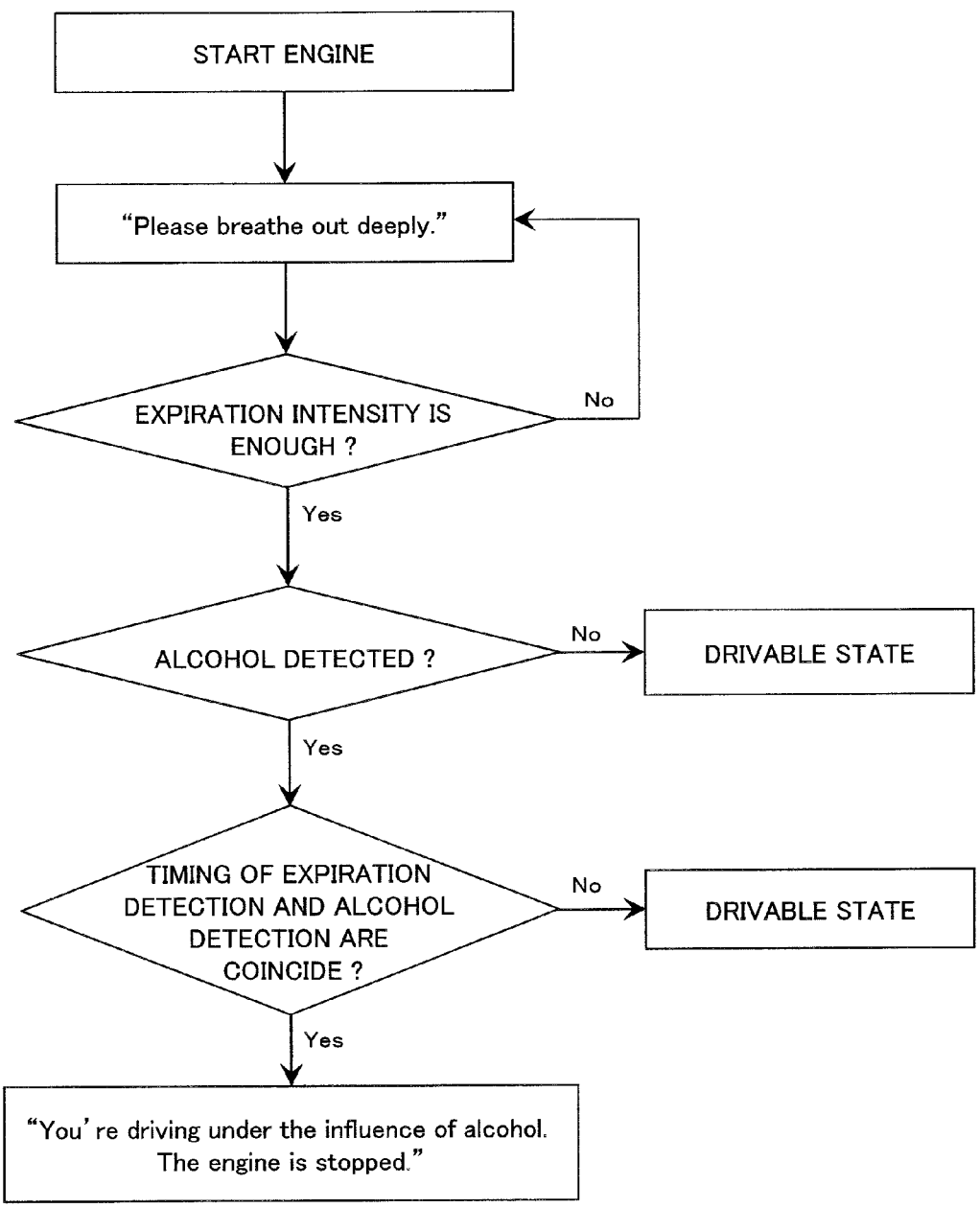
FIG. 19 depicts an alcohol detection algorithm at the time of engine start when the device of the present invention is used.

FIG. 19 depicts an algorithm of a drinking check upon engine start when the present invention is used. After engine start, the driver immediately exhales toward the monitor case 37 for several seconds. Here, to prevent any third parties from interrupting between the driver and the steering wheel, the driver is asked to bring his or her mouth close to the monitor case 37 for detection of a strong expiration peak. A certain threshold for detection of an expiration peak is provided and, if a detected value does not exceed this threshold, the driver is asked to breathe out again. When the strength of the expiration peak is sufficient, the procedure enters an alcohol check. When no alcohol (ethanol) is detected at all, driving is enabled by, for example, setting a shift lever in a movable state. When alcohol (ethanol) is detected, it is determined whether detection of the expiration peak and the detection of the alcohol peak match each other in timing. When they do not match each other, driving is enabled by, for example, setting the shift lever in a movable state. When they match each other, each component is controlled by a control unit provided in the automobile so that driving is disabled by issuing a sound or a voice for confirming whether the state is a drunken state from an in-car loudspeaker or the like, displaying a warning on an in-car monitor, locking the shift lever, stopping the engine, or the like. Then, the procedure enters a test mode, where a final confirmation about drink-driving is performed.

Figure 20:
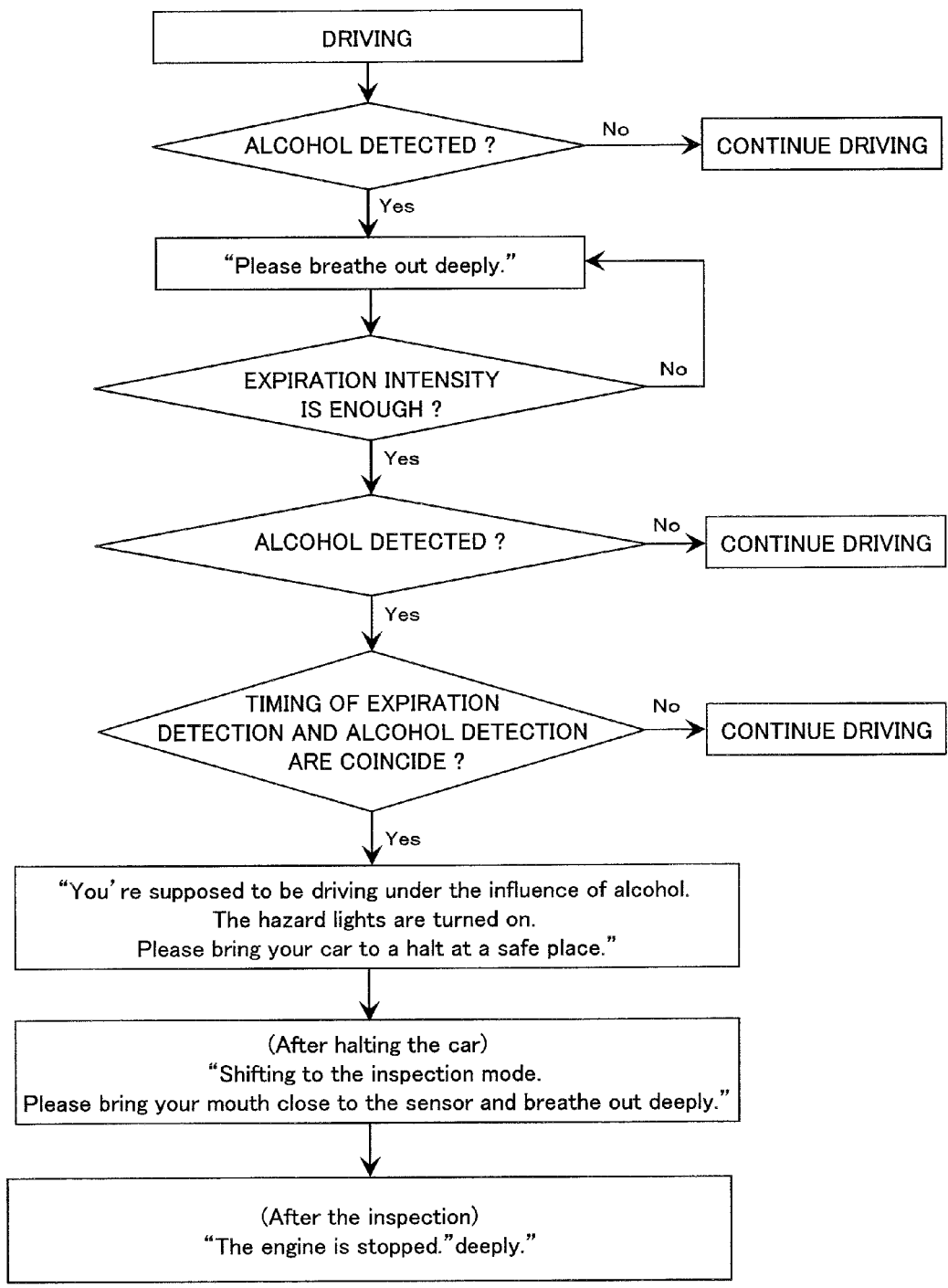
FIG. 20 depicts an alcohol detection algorithm during driving when the device of the present invention is used.

Effectiveness of this device resides in that an alcohol check can be performed even in a driving state. The algorithm at this time is depicted in FIG. 20. During driving, the alcohol sensor is activated to check, always or at predetermined time intervals, whether alcohol is detected. When alcohol is not detected, driving continues as it is. When even a small amount of alcohol is detected, the driver is asked to exhale toward the monitor case 37. As with the case of FIG. 19, a threshold is provided to the strength of the expiration peak, and when the expiration peak and the alcohol peak match each other in timing, attention is called to surrounding vehicles by, for example, flashing a hazard light and, simultaneously, the driver is guided to stop at a safe place. Then, the procedure enters a test mode, where a final confirmation about drink-driving is performed. As described above, compared with an alcohol check scheme of introducing expiration directly to a sensor, in the present invention, an alcohol check during driving can be performed with a simple operation.

Figure 21:
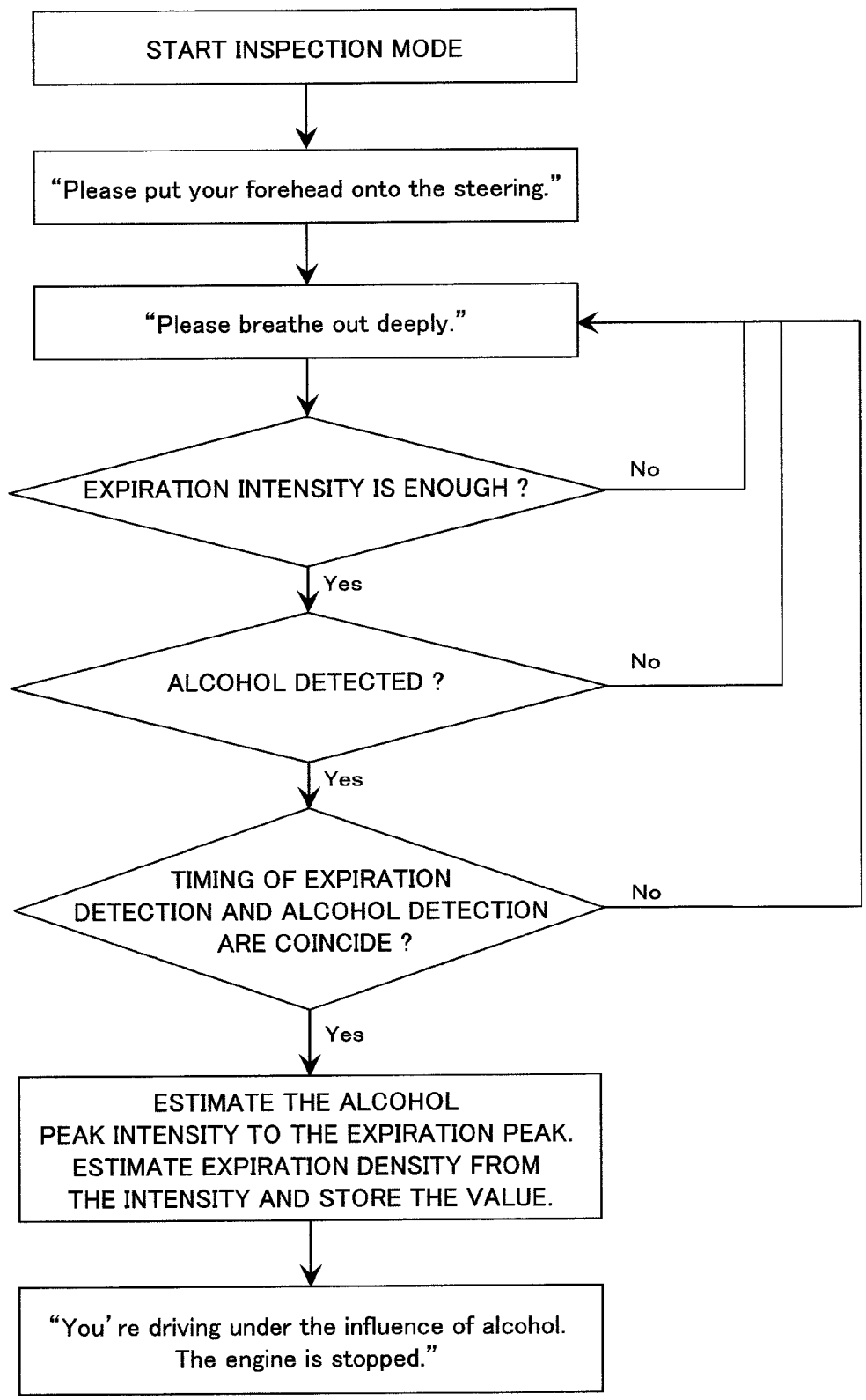
FIG. 21 depicts an alcohol detection algorithm in a test mode when the device of the present invention is used.

FIG. 21 depicts an algorithm of a test mode when the automobile stops. By putting the forehead onto the steering 30, the distance between the mouth of the driver and the monitor case 37 is fixed, and the driver is asked to breathe out several times. If a database of a relation between an expiration peak area and an alcohol peak area with a known concentration is made in advance, the concentration of alcohol in expiration can be estimated from the obtained detection results of the expiration peak and alcohol peak. If this result is recorded in storage means, this is an evidence for drink-driving.

It goes without saying that the alcohol check as described above can be applied not only to drivers of automobiles but also to operators of movable bodies such as motormen of trains and airplane pilots. It is also effective to apply this check to plant operators.

Third Embodiment

Figure 22:
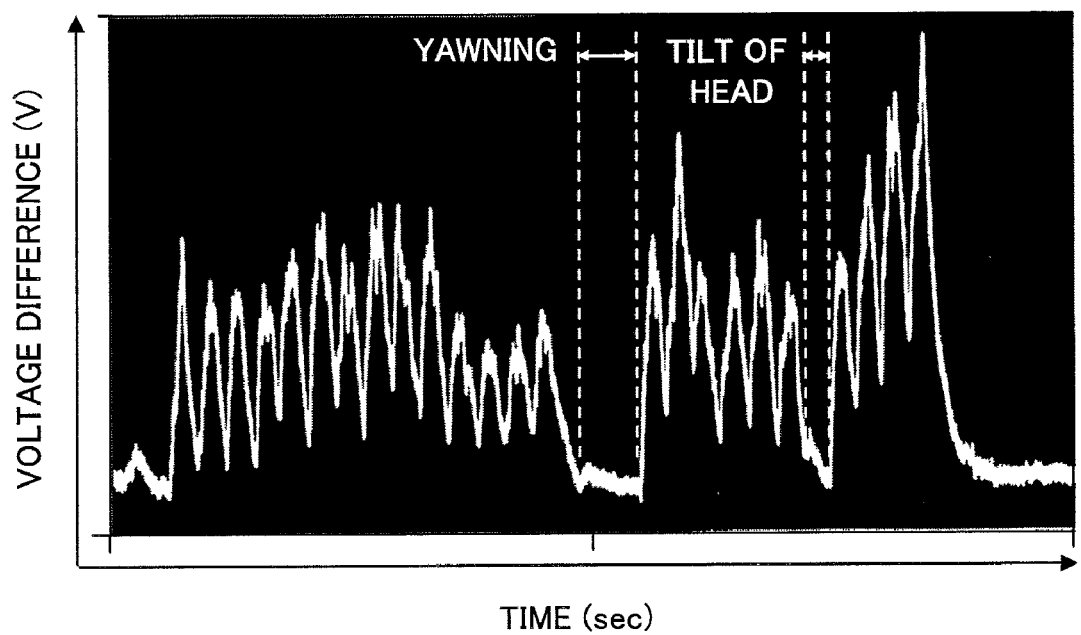
FIG. 22 depicts an example of detection of a change in breathing based on a yawn and a tilt of the head when the device of the present invention is used.

The present invention can also be used for a preventive device for drowsy driving in a movable body such as an automobile. FIG. 22 depicts changes in expiration detection based on a yawn and a tilt of the head (which is referred to herein as an expiration spectrum). When the driver wants to yawn during normal breathing, a change begins to occur in the expiration spectrum before a yawn (a peak based on expiration, that is, an expiration peak, tends to become small). With a yawn, the expiration peak is completely lost during yawning. Also, when the driver becomes drowsy with his or her head started to be tilted, the expiration peak becomes small. With the head significantly tilted, the expiration peak is lost. As such, calculation of an expiration spectrum based on a signal obtained by the sensor and sensing of temporal fluctuations of the expiration peak may be performed by a control unit, computing means may be provided separately, or a computing device may be externally connected.

Figure 23A:
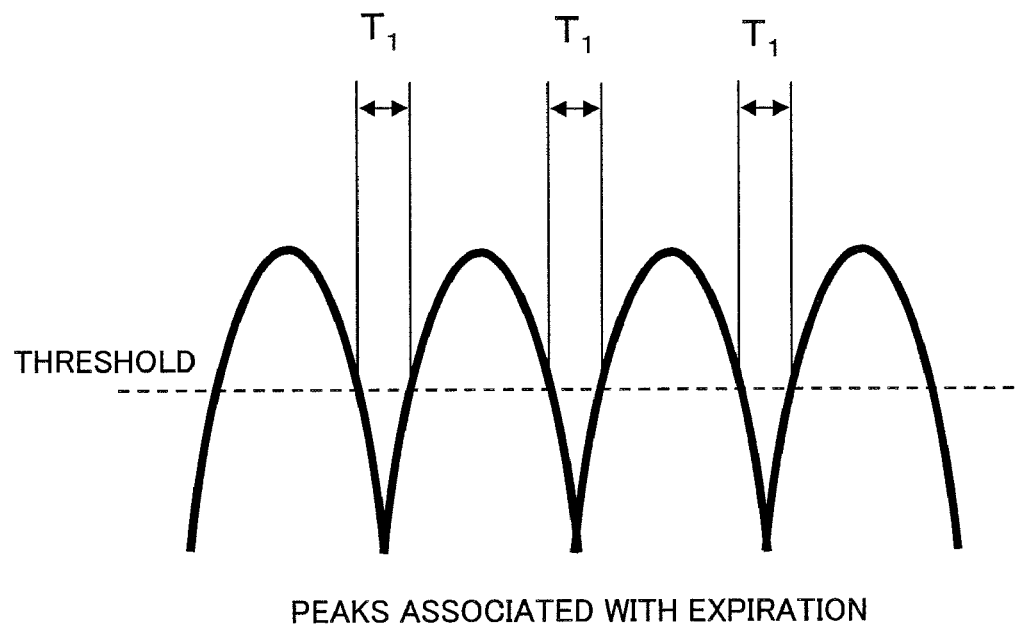
FIGS. 23A and 23B depict the principles of detection of drowsy driving when the device of the present invention is used.
Figure 23B:
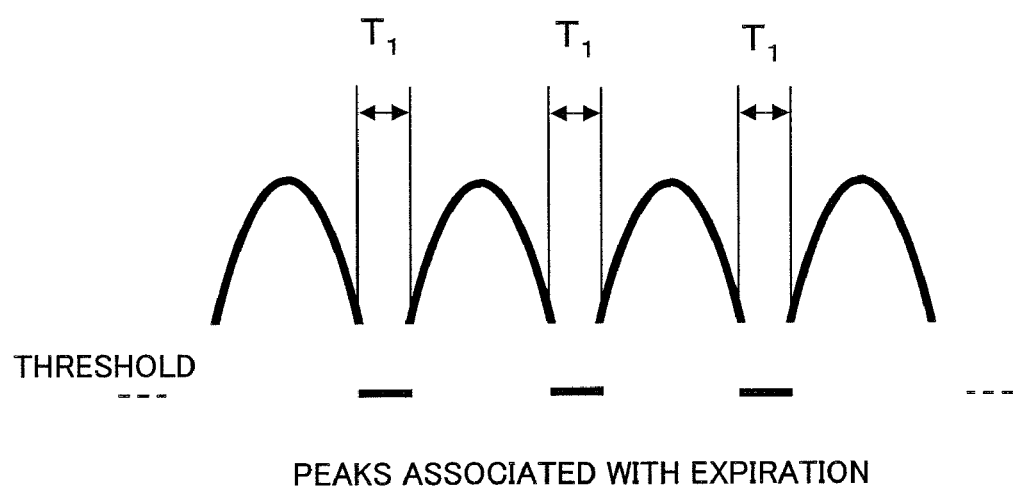
Figure 24:
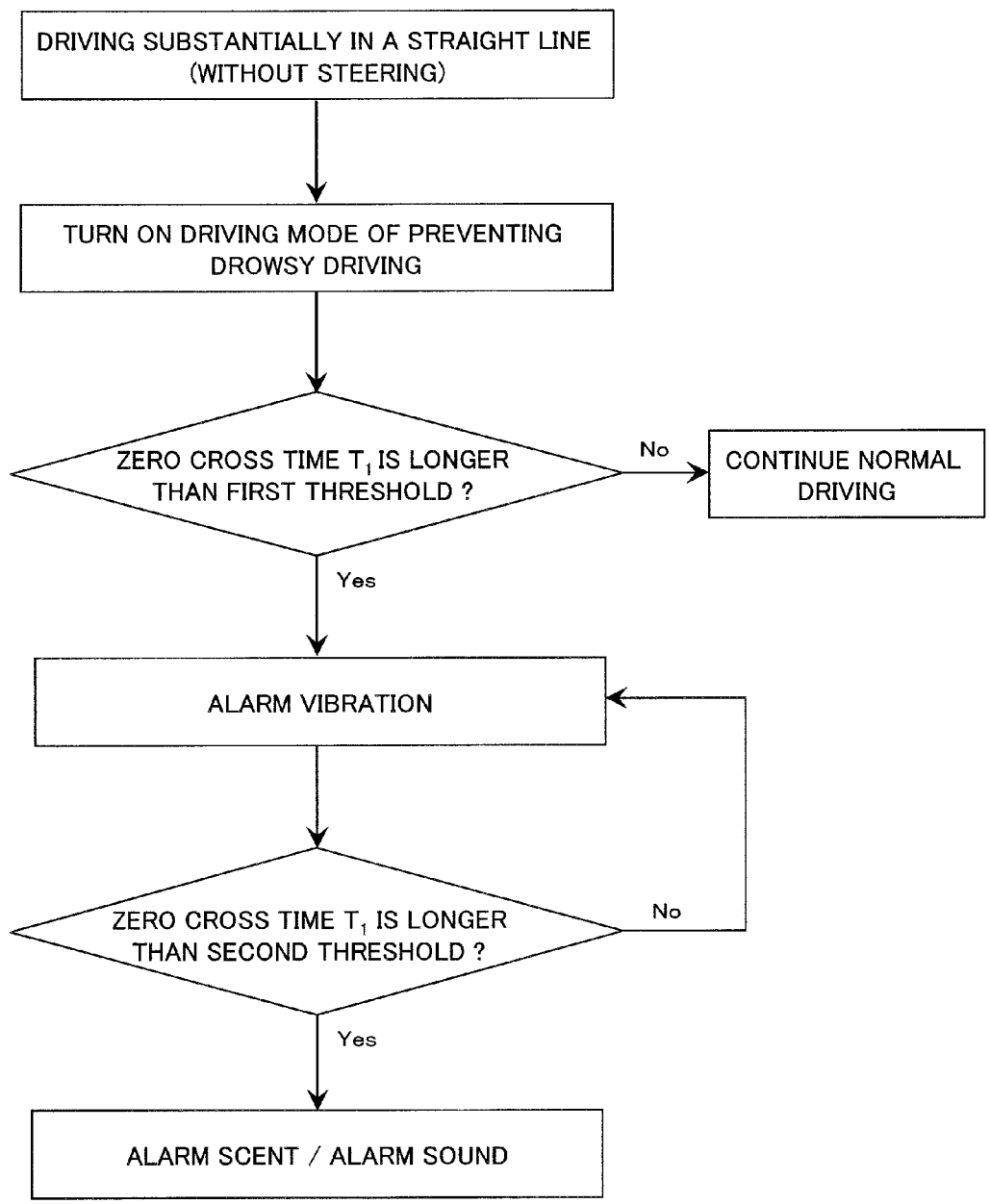
FIG. 24 depicts a drowsy driving detection algorithm when the device of the present invention is used.

By using these characteristics, drowsy driving can be prevented. As depicted in FIGS. 14A and 14B, consider the case in which a preventive device for drowsy driving according to the present invention is disposed on the column cover 39 of the steering wheel 40. In this case, as depicted in FIG. 23A, expiration peaks are observed. When a certain threshold is set individually and a numerical value smaller than that threshold is assumed to be zero, waveforms are as depicted in FIG. 23B. A time when the value becomes zero between expiration peaks (a zero cross time) is about a predetermined time (in this case, $T_1$) if breathing is stable. In this case, with a yawn or a large tilt of the head, the interval between expiration peaks (T) is increased. Thus, when T becomes larger than a predetermined numerical value (a numerical value larger than $T_1$), a warning is set to be issued. Various types of warning can be considered such as flashing a warning lamp, a warning sound, vibrations of the driver's seat for warning, and an odor for warning. FIG. 24 depicts an algorithm for prevention of drowsy driving. In this case, when the driver feels drowsy, this driving mode for prevention of drowsy driving is set to be turned on. Thereafter, the zero cross time is always monitored and, when the time becomes longer than a first threshold, a warning at a first stage (flashing a warning lamp) is set to be performed. When the time further becomes longer than a second threshold, a warning at a second stage (a warning sound, vibrations for warning, and/or an odor for warning) is set to be performed. When the number of times of warning exceeds a predetermined number of times, a message such as "Please take a rest immediately in a safe place" is issued to urge the driver to take a rest.

Figure 25:
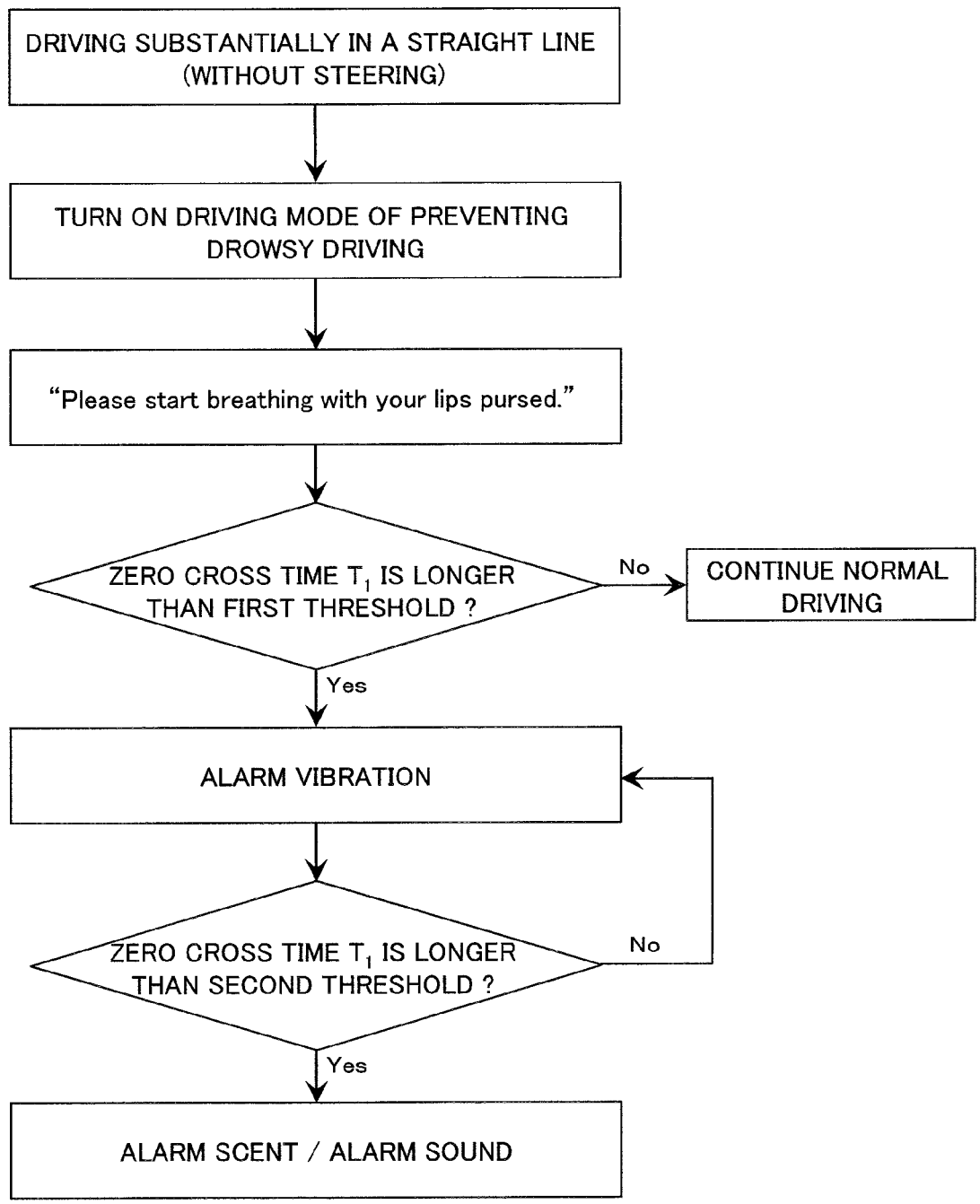
FIG. 25 depicts a drowsy driving detection algorithm (pursed-lip breathing) when the device of the present invention is used.

The algorithm depicted in FIG. 24 focuses attention on breathing, which is an activity under subconsciousness. However, this may miss the time in order to avoid an accident by drowsy driving. To get around this, as depicted in FIG. 25, an activity under consciousness can be incorporated in the algorithm. As an activity under consciousness using the feature of the present invention, there is pursed-lip breathing, which is medically recognized as a breath training method. This is a method of inhaling from the nose with the mouth lightly closed and then breathing out with the mouth pursed. After the driving mode for prevention of drowsy driving is turned on, the driver is asked to start pursed-lip breathing. When the expiration peak is below the threshold, a warning is issued as depicted in FIG. 25. This uses the fact that an activity under consciousness is degraded by drowsiness. Drowsiness can be detected at a temporally earlier stage than that when normal breathing is detected in an activity under subconsciousness, which is desirable from a viewpoint of preventing an accident by drowsy driving.

Figure 26:
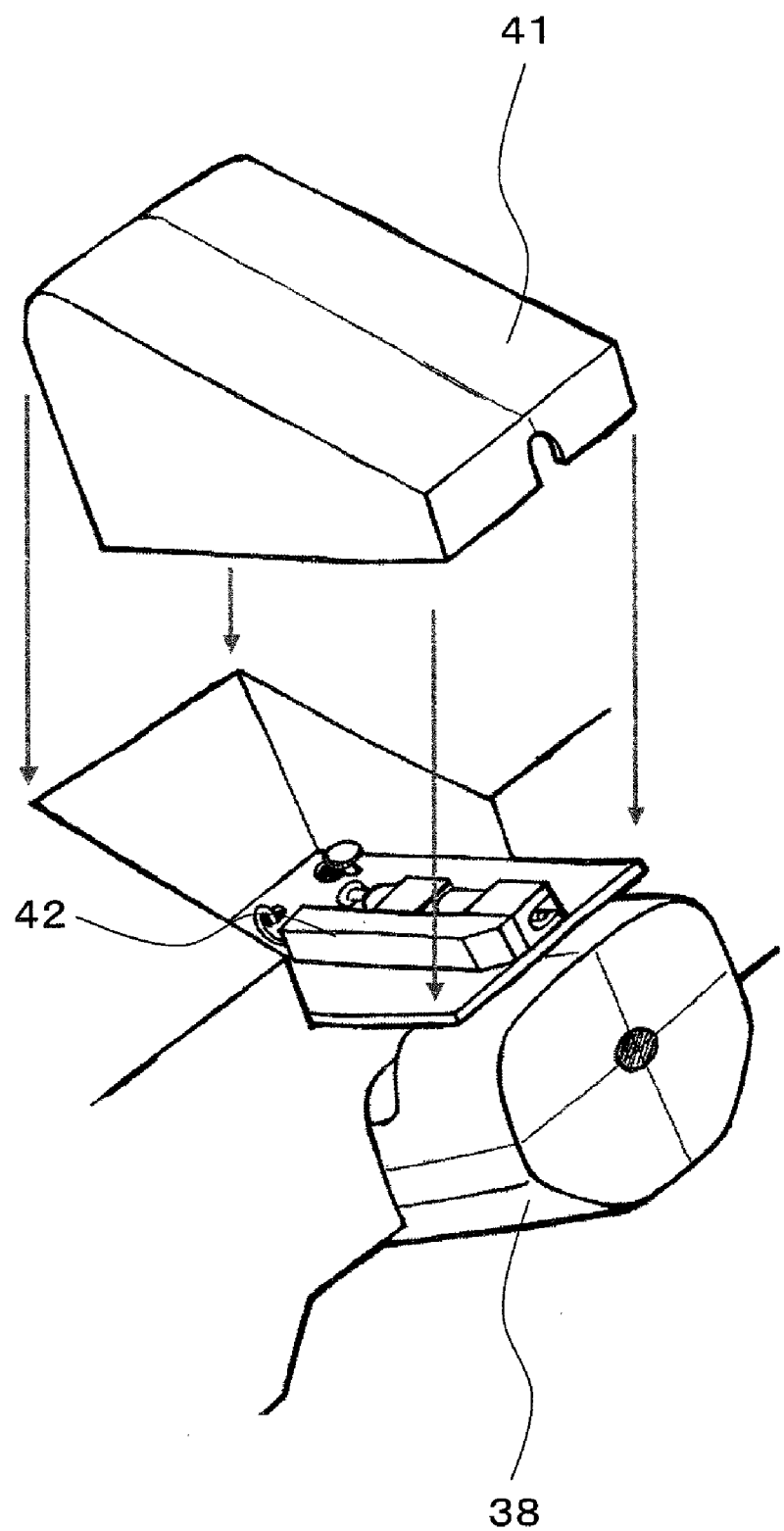
FIG. 26 depicts an odor generator in the present invention.

However, as depicted in FIGS. 14A and 14B, when the preventive device for drowsy driving according to the present invention is disposed near the steering wheel 40, when the steering wheel 40 is steered sharply, it becomes difficult to detect expiration, and therefore fluctuations of the expiration peak in this case are required to be neglected. Therefore, the preventive device for drowsy driving according to the present invention is required to be in conjunction with steering wheel driving information. In consideration of the fact that the undrunken driver tends to get drowsy often at the time of linear, monotonous driving such as driving on an expressway, the present invention is also effective for prevention of drowsy driving. FIG. 26 depicts an example of a system emitting a warning odor, in which an odor generating device 42 covered with a cover 41 is disposed near a column cover 38 and when a catnap is detected by the method described above, a slightly irritating odor is generated toward the driver, which is effective for the driver to be awaken.

It goes without saying that the drowsy-driving check as described above can be applied not only to drivers of automobiles but also to operators of movable bodies such as motormen of trains and airplane pilots. It is also effective to apply this check to plant operators.

Fourth Embodiment

Figure 27:
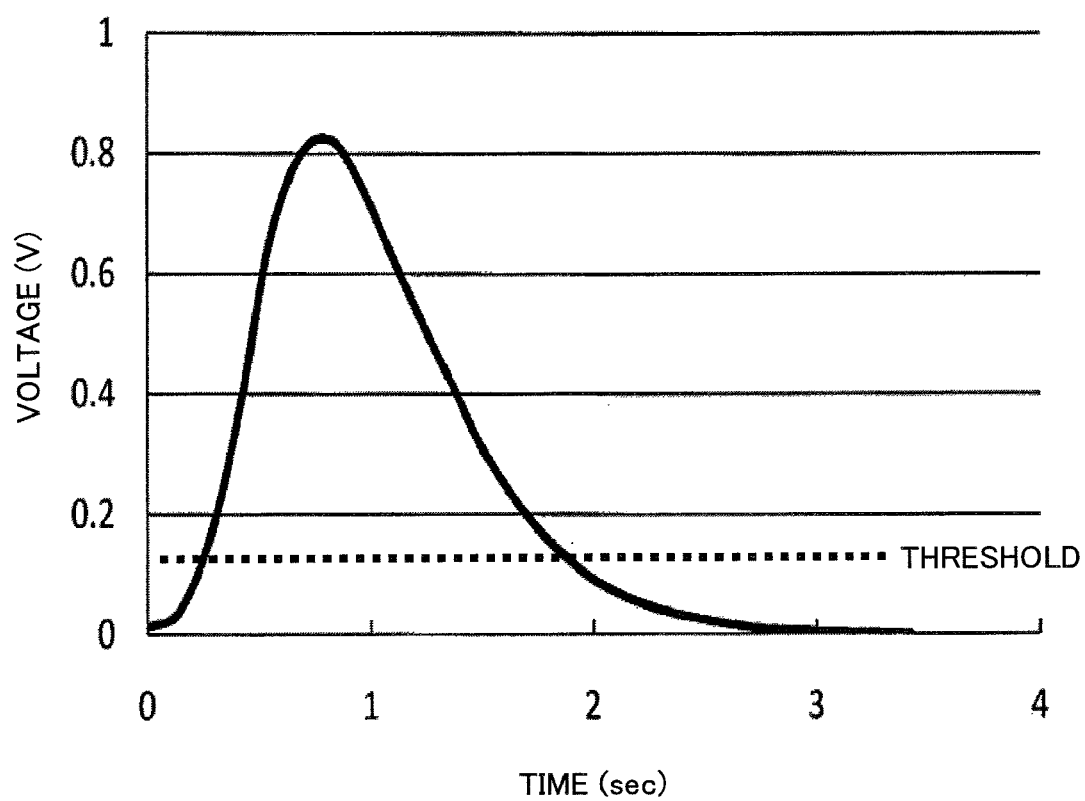
FIG. 27 depicts the principles of device operation when the device of the present invention is used.

The present invention can also be used for an interface for operating a device in a non-contact manner. FIG. 27 depicts an example in which one expiration has been detected. Here, a threshold is set in advance for a signal value to be obtained and, the power supply of the device is set in advance to be turned on when a signal value equal to or larger than this threshold is detected. This allows usage as an interface for operating a device in a non-contact manner. At the expiration peak according to the present invention, the signal strength is attenuated within about several seconds, and therefore responsiveness is also good.

Figure 28A:
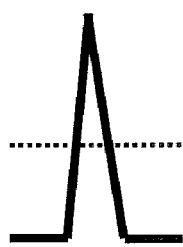
FIGS. 28A to 28E depict a device operation command when the device of the present invention is used.
Figure 28B:
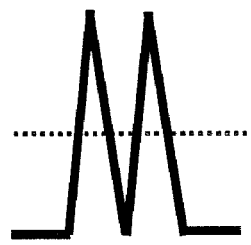
Figure 28C:
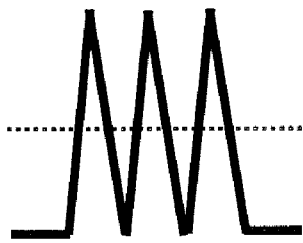
Figure 28D:
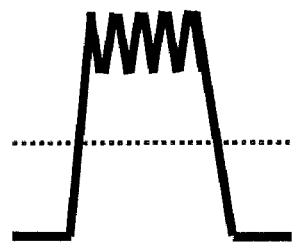
Figure 28E:
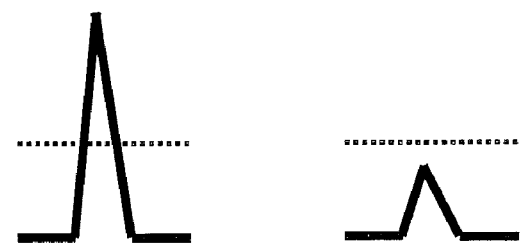

As a command for a device interface, an example depicted in FIGS. 28A to 28E can be considered. FIG. 28A depicts the case of one expiration, FIG. 28B depicts the case of two expirations, and FIG. 28C depicts the case of three expirations. These are the cases in which a different command is applied depending on the number of times of expiration. Also, as in FIG. 28D, a different command can be applied depending on the time during which a plurality of expirations are let out exceeding the threshold. Furthermore, as depicted in FIG. 28E, a different command can be applied by using a combination of expirations with different strengths (in this case, a combination of a strong expiration and a weak expiration).

Figure 29:
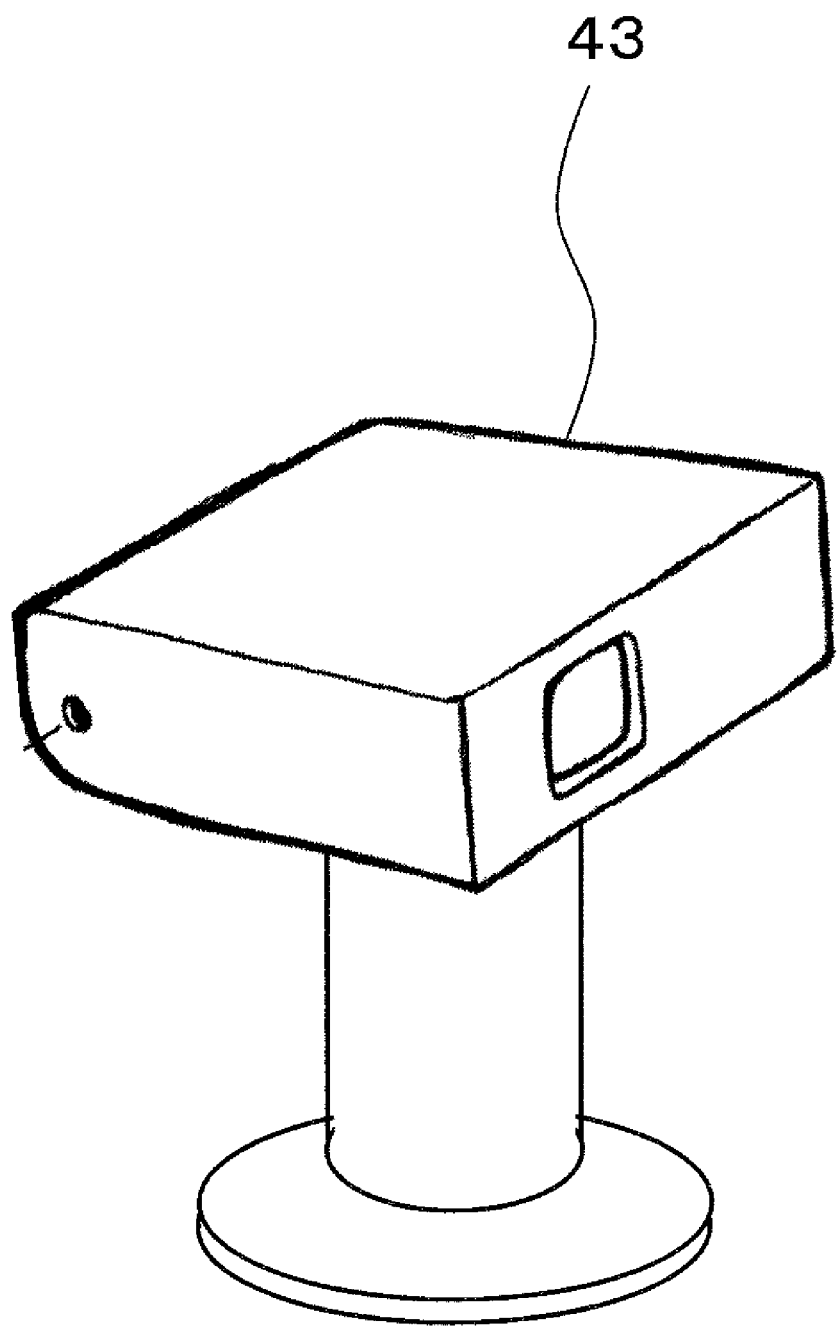
FIG. 29 depicts a device interface in the present invention.
Figure 30:
FIG. 30 depicts an example of the device interface in the present invention.
Figure 31:
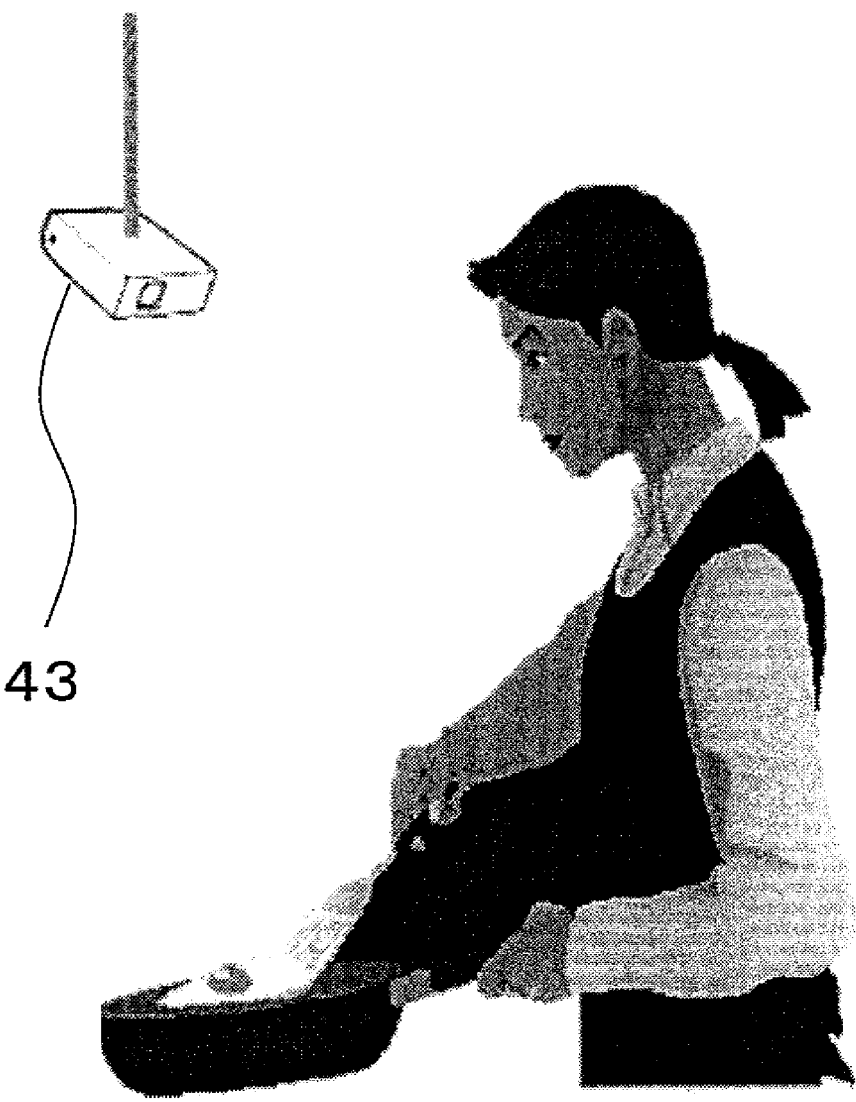
FIG. 31 depicts an example of the device interface in the present invention.
Figure 32:
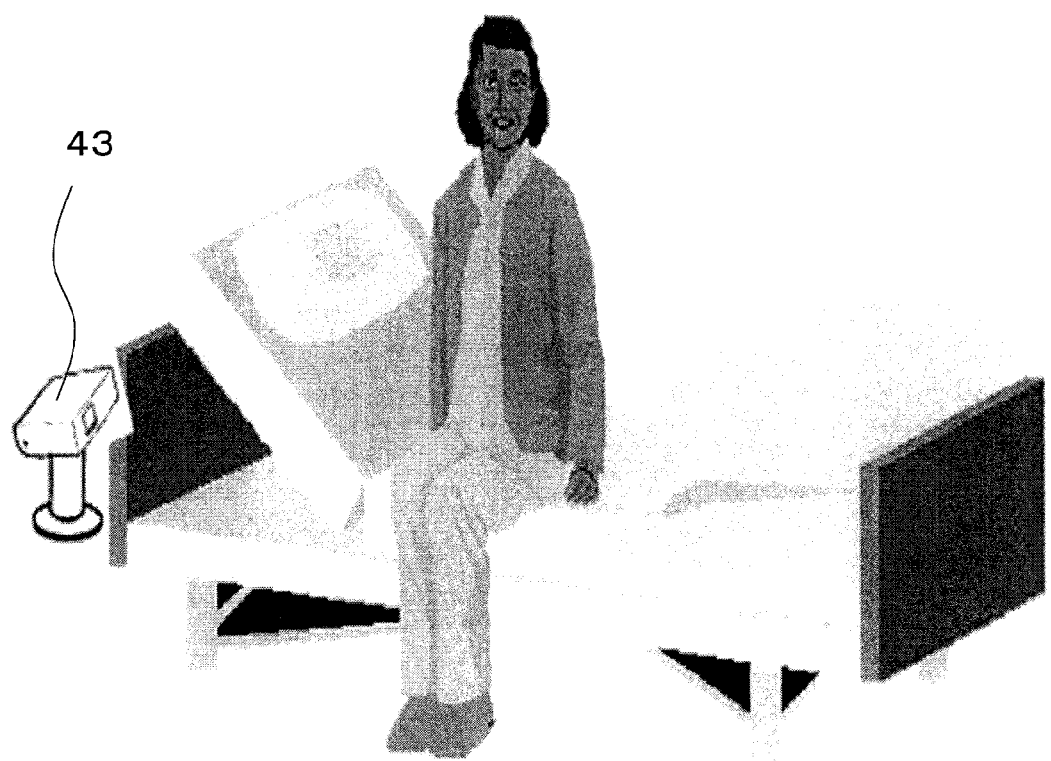
FIG. 32 depicts an example of the device interface in the present invention.

With the use of the device interface 42 using the present invention as in FIG. 29, there are various usage scenes such as 1) the case in which, at the time of making a call by using a portable phone in a movable body such as an automobile, a call is turned on/off or the volume is turned up/down, 2) the case in which a device is desirably operated in a non-contact manner in view of sanitation in a medical institution such as a hospital, and 3) the case in which a hand-impaired person or an elderly person operates a device at home (such as a switch for television or a switch for light). Note that it is also good for health for elderly people to routinely operate a device by using this interface based on breathing because breathing at a certain level or higher is repeated. FIG. 30 depicts an example of operation of a personal computer (such as an on/off operation of the power supply and addition of another operation during typing on the keyboard with both hands), FIG. 31 depicts an example of operation when the hands are busy with cooking or the like (such as handling of telephone and operation of another household electric appliance), and FIG. 32 depicts an example of operation assist for physically-challenged people (operation of a bed and operation of a digital device).

Fifth Embodiment

In consideration of responsiveness when air with the same humidity is introduced, by detecting a difference in peak strength at the time of continuous breathing and analyzing fluctuations in peak difference with a computing unit or a control unit, the quality of breathing (a difference in humidity between abdominal breathing and costal breathing) is represented in addition to fluctuations in distance between the mouth and a detector. With the use of the peak difference, the state of the user can be grasped. When the current state of breathing is displayed on a monitor or the like by using an externally connected device or the like separately provided and an ideal breathing state stored in advance is read from memory or the like for display, the present invention can be utilized for a breath training method or a breathing game in which a score is received based on the quality of breathing.

Sixth Embodiment

By using the device depicted in FIG. 25, liquid or gas generated from a finger can be detected. In particular, when sweat from a finger is introduced and generated water clusters are introduced to an alcohol detector, alcohol can be easily detected. Here, by combining with finger vein authentication, alcohol can be detected with the person identified, which is effective for preventing drink-driving.

Specifically, a finger authentication device can be configured in a manner such that an opening is provided to a placing unit where a finger is placed so that moisture coming from the surface of the living body can be detected and an optical axis of an ion beam is disposed in a direction substantially parallel to the surface for placing the finger so that a deflected ion beam is detected. Here, a light source and imaging unit are required to be disposed at positions where light and a camera required for imaging the finger are not affected by the ion beam. An example of arrangement is such that the light source is disposed at a position upper than the position of the finger and the imaging unit is disposed immediately below the opening of the finger placing unit. Another example is opposed arrangement so that light from the light source is not entirely shielded by the detection electrode. The arrangement is not restricted to these, and the light source and the imaging unit, and the detection electrode can be arranged as long as light from the light source to the finger is not entirely shielded.

Note that the orientation of the optical axis of the ion beam is not necessarily required to be approximately parallel to the placing surface, and the arrangement can be any as long as it does not affect shooting an authentication image.

Seventh Embodiment

In addition to the device depicted in FIGS. 11A and 11B, when a device for continuously introducing gas from a liquid sample (for example, a syringe pump) is combined, various components in gas can be accurately measured. Here, when the entire device is put in a box with temperature and humidity controlled, clusters with substantially the same particle diameter distribution can always be generated, thereby significantly improving detection accuracy. In the examples described above, the case of alcohol detection using a semiconductor sensor has mainly been described. In the example of FIGS. 11A and 11B, the alcohol sensor unit 31 can be removed. Therefore, for the expiration monitor unit 30, the type of semiconductor sensor can be changed, and detectors with another principle can be used such as measurement of changes in corona discharge voltage under a constant-current condition and measurement of electric conductivity, thereby allowing measurement of various types of substances.

Industrial Applicability

The present invention can be used for expiration detection in a non-contact and noninvasive manner. The present invention can also be used for a preventive device for drink-driving and a preventive device for drowsy driving in a movable body such as an automobile. Also, the present invention can be used for an interface for operating a device in a non-contact manner. Furthermore, the present invention can be used as a breath training device and an analysis preprocessor.

Description of References

1 Sensor Unit
2 Needle Electrode for Corona Discharge
3 Holder Presser
4 Needle Electrode for Corona Discharge Holder
5 Counter Electrode
6 Detection Electrode
7 Stop Electrode
8 Sensor Unit Lid
9 Support for Counter Electrode
10 Support for Detection Electrode
11 First Exhaust-port Joint
12 Second Exhaust-port Joint
13 Exhaust Port for Ion Source Unit
14 Expiration Introduction Port
15 Expiration Discharge Port
16 Second Expiration Discharge Port
17a Mesh Plate for Expiration Introduction Port
17b Mesh Plate for Expiration Discharge Port
18 First Expiration Discharge Port
19 Second Expiration Discharge Port
20 Joint for Exhausting Ion Source Unit
21 High Voltage Power Supply for Needle Electrode
22 High Voltage Power Supply for Counter Electrode
23 Amplifier for Detection Electrode
24 Power Supply for Alcohol Sensor
25 Alcohol Sensor
26 Sensor Box
27 Display
28 Expiration Introduction Port for Sensor Box
29 Switch
30 Expiration Monitor Unit
31 Alcohol Sensor Unit
32a, 32b, 32c Connector
33 Alcohol Sensor Head
34 Sensor Control Board
35 Sensor Control Line
36a, 36b Signal Line
37a, 37b Monitor Case
38a Base
39 Column Cover
40 Steering Wheel
41 Cover
42 Odor Generator
43 Device Interface

The invention claimed is:

1. An ion detector having a casing inside of which is under an atmospheric pressure environment, the ion detector comprising:
   inside of the casing,
   an ion source generating an ion beam;
   a counter electrode having an opening that lets the ion beam pass;
   introducing means for introducing outside air into the inside of the casing; and
   a detection electrode detecting ions deflected by a reaction between the outside air introduced by the introducing means into the inside of the casing and the ion beam.

2. The ion detector according to claim 1, comprising
   control means for generating a potential difference between the counter electrode and the detection electrode.

3. The ion detector according to claim 1, wherein
   the ion source has a needle electrode and means for applying a high voltage to the needle electrode.

4. The ion detector according to claim 1, comprising
   exhaust means for preventing residence of the outside air into the inside of the casing.

5. The ion detector according to claim 1, wherein
   the outside air is expiration.

6. An ion detector with a casing inside of which is under an atmospheric pressure environment, the ion detector comprising:
   inside of the casing,
   an ion source generating an ion beam;
   a counter electrode having an opening in a direction of an axis of irradiation of the ion beam;
   introducing means for introducing outside air into the inside of the casing; and
   a detection electrode detecting ions deflected by a reaction between the outside air introduced by the introducing means into the inside of the casing and the ion beam,
   the detection electrode having a first opening on the axis of irradiation of the ion beam and further having a second opening at a position different from the axis of irradiation of the ion beam.

7. The ion detector according to claim 6, comprising
   a sensor detecting ions passing through the second opening.

8. The ion detector according to claim 7, wherein
   the sensor is an alcohol sensor.

9. The ion detector according to claim 6, comprising
   computing means for calculating an expiration spectrum based on a detection signal detected by the detection electrode.

10. The ion detector according to claim 9, wherein
    a peak of expiration is specified from the expiration spectrum and
    a change of the expiration peak with time is detected.

* * * * *